US007312288B2

(12) United States Patent
Kinsho et al.

(10) Patent No.: US 7,312,288 B2
(45) Date of Patent: Dec. 25, 2007

(54) POLYMERIZABLE FLUORINATED ESTER COMPOUNDS AND THEIR PREPARING PROCESSES

(75) Inventors: Takeshi Kinsho, Niigata-ken (JP); Takeru Watanabe, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 426 days.

(21) Appl. No.: 10/958,373

(22) Filed: Oct. 6, 2004

(65) Prior Publication Data

US 2007/0249858 A1    Oct. 25, 2007

(30) Foreign Application Priority Data

Oct. 7, 2003    (JP)    ............................. 2003-348104

(51) Int. Cl.
*C07C 69/52*    (2006.01)
*C07C 21/18*    (2006.01)
*C07C 19/08*    (2006.01)
*C07C 25/00*    (2006.01)
*C07C 17/00*    (2006.01)

(52) U.S. Cl. ...................... 526/245; 570/136; 570/142; 570/182; 570/186

(58) Field of Classification Search ................ 570/142, 570/136, 182, 183; 526/245, 246
See application file for complete search history.

(56) References Cited

U.S. PATENT DOCUMENTS

| 2002/0009668 | A1 | 1/2002 | Nishimura et al. |
| 2003/0078352 | A1 | 4/2003 | Miyazawa et al. |
| 2003/0157430 | A1 | 8/2003 | Yoon et al. |
| 2004/0192867 | A1* | 9/2004 | Narita et al. ................ 526/242 |

FOREIGN PATENT DOCUMENTS

| JP | 2002-072484 A | 3/2002 |
| JP | 2003-040840 A | 2/2003 |
| JP | 2003-192729 A | 7/2003 |

OTHER PUBLICATIONS

G. Wallraff et al., "Active Fluororesists for 157nm lithography in 2nd International Symposium on 157 nm Lithography" May 14-17, 2001.

T. Nakai et al., "Perfluoro-Enolate Chemistry: Facile Generation and Unique Reactivitires of Metal F-1-Propen-2-Olates," Tetrahedron Letters, vol. 29, No. 33, pp. 4119-4122, (1998).

T. Nakai et al., Organic Syntheses, vol. 76, pp. 151-157, (1998).

* cited by examiner

*Primary Examiner*—Yvonne Eyler
*Assistant Examiner*—MLouisa Lao
(74) *Attorney, Agent, or Firm*—Birch, Stewart, Kolasch & Birch, LLP

(57) ABSTRACT

Polymerizable fluorinated ester compounds having formulae (1) and (2) are novel wherein $R^1$ is H, methyl or trifluoromethyl, $R^2$ and $R^3$ are H or a monovalent hydrocarbon group, $R^2$ and $R^3$ may form a ring, $R^4$ is H, OH or a monovalent hydrocarbon group, and $R^5$ is an acid labile group. They are useful as monomers to produce polymers for the manufacture of radiation-sensitive resist compositions which have high transparency to radiation having a wavelength of up to 500 nm and exhibit good development properties due to the presence of phenol-like acidic hydroxyl groups

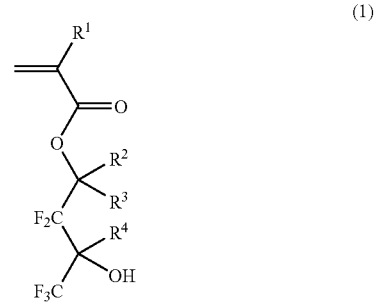

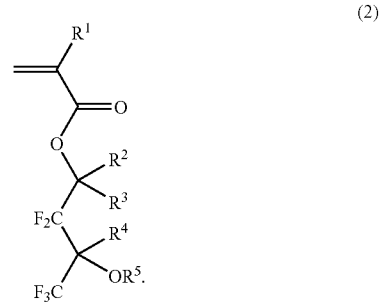

5 Claims, No Drawings

POLYMERIZABLE FLUORINATED ESTER COMPOUNDS AND THEIR PREPARING PROCESSES

CROSS-REFERENCE TO RELATED APPLICATION

This non-provisional application claims priority under 35 U.S.C. §119(a) on Patent Application No. 2003-348104 filed in Japan on Oct. 7, 2003, the entire contents of which are hereby incorporated by reference.

TECHNICAL FIELD

This invention relates to novel polymerizable fluorinated ester compounds and processes for preparing the same. The polymerizable fluorinated ester compounds are useful as raw materials for the synthesis of polymers, functional materials, pharmaceutical and agricultural chemicals, and most useful as monomers to produce polymers for the manufacture of radiation-sensitive resist compositions which are fully transparent to radiation having a wavelength of up to 500 nm, especially up to 200 nm, typically ArF and $F_2$ laser beams, and have good resistance to dry etching.

BACKGROUND ART

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF, ArF or $F_2$ laser as the light source is strongly desired to reach the practical level as the micropatterning technique capable of achieving a feature size of 0.3 μm or less. Various alkali-soluble resins are used as the base resin in such resists.

For KrF laser resists, a polyhydroxystyrene resin having phenolic hydroxyl groups as the alkali-soluble functional group is, in fact, a standard base resin. For ArF laser resists, poly(meth)acrylate resins and resins comprising polymerized units of cycloaliphatic olefin such as norbornene, using carboxyl groups as the alkali-soluble group, are under investigation. Of these, the poly(meth)acrylate resins are regarded, due to ease of polymerization, as a promising candidate for practical use. These resist resins using carboxyl groups as the alkali-soluble functional group, having a higher acidity than phenolic hydroxyl groups, however, tend to encounter difficulty of dissolution control, often leading to pattern collapse caused by swelling or the like.

Functional groups having an acidity comparable to phenolic hydroxyl groups are desired. It was proposed to use an alcohol having plural fluorine atom substitution at α- and α'-positions (e.g., having a partial structure: —C(CF$_3$)$_2$OH) as the alkali-soluble functional group, as described in G. Wallraff et al., Active Fluororesists for 157 nm lithography in 2nd International Symposium on 157 nm Lithography. Styrene and norbornene derivatives having fluoroalcohol —C(CF$_3$)$_2$OH incorporated therein are proposed as monomers used in the manufacture of base resins. Similar examples of fluoroalcohol-substituted norbornene are found in JP-A 2003-192729 and JP-A 2002-72484. For the polymerization of norbornene monomers, however, radical polymerization of monomers of the same type is difficult, and instead, special polymerization techniques such as coordinate polymerization and ring-opening metathesis polymerization, using unique transition metal catalysts are necessary. Although alternating copolymerization of a norbornene monomer with a comonomer such as maleic anhydride or maleimide can be performed by radical polymerization, the presence of comonomer imposes a substantial limit on the freedom of resin design.

JP-A 2003-040840 describes fluoroalcohol-substituted acrylate monomers. Although the method of preparing these monomers is not definite, the starting material used is hexafluoroacetone (boiling point −27° C.) which is awkward to handle because it is gaseous at room temperature. The synthesis of polymerizable compound must follow long steps, leaving the problem that commercial preparation is difficult.

There is a strong demand to develop an easily prepared polymerizable compound having both a (meth)acrylate structure that facilitates polymerization or making a resist resin and a functional group that has an acidity comparable to phenolic hydroxyl.

SUMMARY OF THE INVENTION

An object of the invention is to provide novel polymerizable fluorinated ester compounds which are useful as monomers to produce resist base resins that are fully transparent to radiation having a wavelength of up to 500 nm, especially up to 200 nm, and have good development properties and good resistance to dry etching and which can be prepared from readily available raw materials. Another object is to provide processes for preparing the same.

The inventor has found that polymerizable fluorinated ester compounds having the general formulae (1) and (2) can be readily prepared in high yields from readily available raw materials by the processes to be described later; that these compounds are polymerizable by industrially applicable methods such as radical polymerization; and that the use of resins resulting from polymerization of the ester compounds offers radiation-sensitive resist materials having improved transparency at wavelength 200 nm or less, improved etching resistance and good development properties.

In one aspect, the invention provides a polymerizable fluorinated ester compound having the general formula (1) or (2).

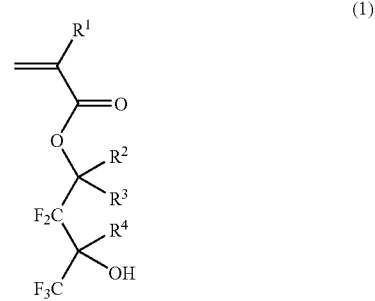

(1)

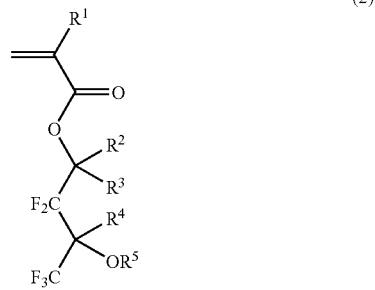

(2)

Herein $R^1$ is hydrogen, methyl or trifluoromethyl, $R^2$ and $R^3$ are each independently hydrogen or a monovalent hydrocarbon group of 1 to 15 carbon atoms which may contain at least one hetero atom, a pair of $R^2$ and $R^3$ may bond together to form a ring with the carbon atom to which they are bonded, and each of $R^2$ and $R^3$ is a divalent hydrocarbon group of 1 to 15 carbon atoms which may contain at least one hetero atom when they form a ring, $R^4$ is hydrogen, hydroxyl, or a monovalent hydrocarbon group of 1 to 15 carbon atoms which may contain at least one hetero atom, and $R^5$ is an acid labile group.

In another aspect, the invention provides processes for preparing polymerizable fluorinated ester compounds.

A first embodiment is a process for preparing a polymerizable fluorinated ester compound having the general formula (1), comprising the steps of reacting a ketoalcohol compound having the general formula (3) with a compound of the general formula: $R^4$—Z to form a diol compound having the general formula (4), and acylating the diol compound to form a polymerizable fluorinated ester compound having the general formula (1).

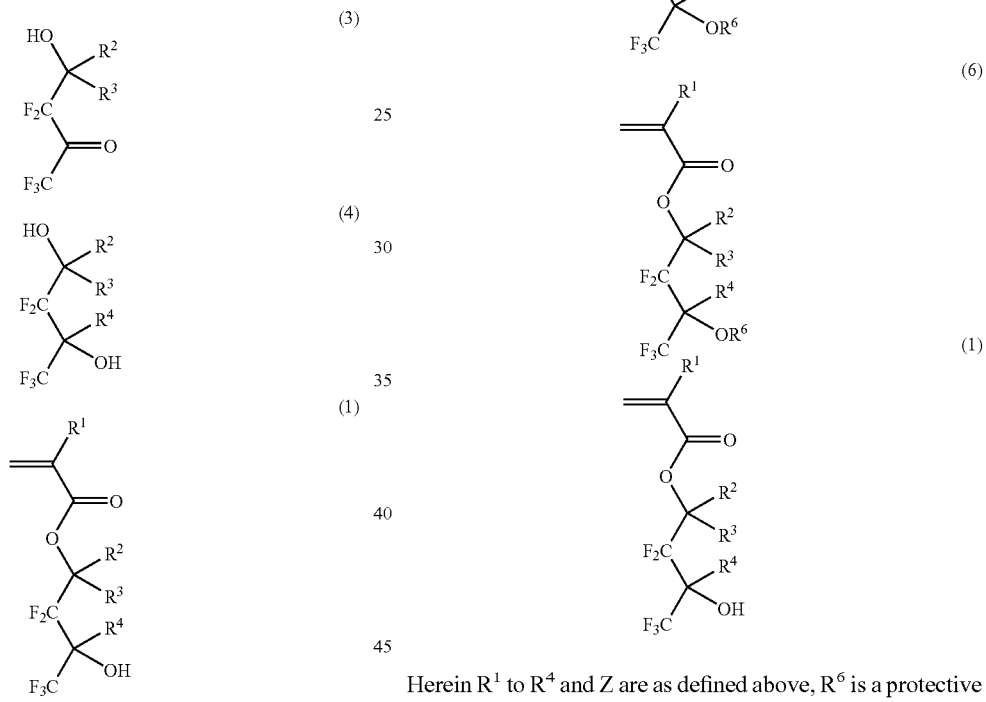

Herein $R^1$ to $R^4$ are as defined above, and Z is such a monovalent group that $R^4$—Z provides a $R^4$ anion equivalent.

A second embodiment is a process for preparing a polymerizable fluorinated ester compound having the general formula (1), comprising the steps of reacting a ketoalcohol compound having the general formula (3) with a compound of the general formula: $R^4$—Z to form a diol compound having the general formula (4), protecting one of the two hydroxyl groups of the diol compound to form an alcohol compound having the general formula (5), acylating the alcohol compound to form a protected polymerizable fluorinated ester compound having the general formula (6), and deprotecting the compound of formula (6) into a polymerizable fluorinated ester compound having the general formula (1).

Herein $R^1$ to $R^4$ and Z are as defined above, $R^6$ is a protective group.

A third embodiment is a process for preparing a polymerizable fluorinated ester compound having the general formula (2), comprising the steps of reacting a ketoalcohol compound having the general formula (3) with a compound of the general formula: $R^4$—Z to form a diol compound having the general formula (4), protecting one of the two hydroxyl groups of the diol compound with an acid labile group to form an alcohol compound having the general formula (7), and acylating the alcohol compound to form a polymerizable fluorinated ester compound having the general formula (2).

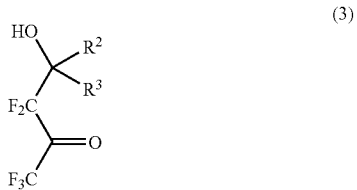

-continued (4)
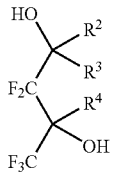

(7)
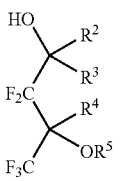

(2)
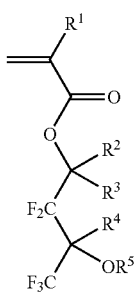

Herein $R^1$ to $R^5$ and Z are as defined above.

A fourth embodiment is a process for preparing a polymerizable fluorinated ester compound having the general formula (2), comprising the step of protecting a polymerizable fluorinated ester compound having the general formula (1) with an acid labile group to form a polymerizable fluorinated ester compound having the general formula (2).

(1)
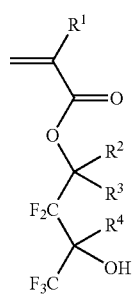

(2)
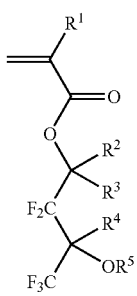

Herein $R^1$ to $R^5$ are as defined above.

The polymerizable fluorinated ester compounds of the invention are novel. They are useful as raw materials for the synthesis of polymers, functional materials, pharmaceutical and agricultural chemicals. They are most useful as monomers to produce polymers for the manufacture of radiation-sensitive resist compositions which have high transparency to radiation having a wavelength of up to 500 nm, especially up to 200 nm, and exhibit good development properties due to the presence of phenol-like acidic hydroxyl groups.

DESCRIPTION OF THE PREFERRED EMBODIMENTS

In the first embodiment, the polymerizable fluorinated ester compounds of the invention have the general formula (1) or (2).

(1)
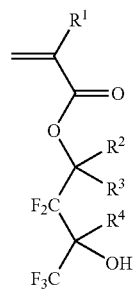

(2)
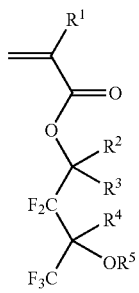

Herein $R^1$ is hydrogen, methyl or trifluoromethyl.

$R^2$ and $R^3$ are each independently hydrogen or a monovalent hydrocarbon group of 1 to 15 carbon atoms which may contain at least one hetero atom. Suitable monovalent hydrocarbon groups of 1 to 15 carbon atoms which may contain at least one hetero atom include straight, branched or cyclic alkyl groups such as methyl, ethyl, propyl, isopropyl, butyl, sec-butyl, tert-butyl, tert-amyl, pentyl, hexyl, octyl, nonyl, decyl, cyclopropyl, cyclobutyl, cyclopentyl, cyclohexyl, cyclopentylmethyl, cyclopentylethyl, cyclopentylbutyl, cyclohexylmethyl, cyclohexylethyl, and cyclohexylbutyl; aryl groups such as phenyl, methylphenyl, naphthyl, anthryl, and phenanthryl; and aralkyl groups such as benzyl, diphenylmethyl and phenethyl. In the foregoing groups, some hydrogen atoms may be substituted with halogen atoms, alkyl groups, aryl groups, alkoxy groups, alkoxycarbonyl groups, oxo groups or the like. A pair of $R^2$ and $R^3$ may bond together to form a ring with the carbon atom to which they are bonded. In that event, $R^2$ and $R^3$ each stand for a divalent hydrocarbon group of 1 to 15 carbon atoms which may contain at least one hetero atom. Suitable rings formed by $R^2$ and $R^3$ include cyclopropane, cyclobutane, cyclopentane, cyclohexane, bicyclo[2.2.1]heptane, bicyclo[2.2.2]octane, tricyclo[5.2.1.0$^{2,6}$]decane, and adamantane. In these rings, some hydrogen atoms may be substituted with halogen atoms, alkyl groups, aryl groups, alkoxy groups, alkoxycarbonyl groups, oxo groups or the like.

$R^4$ is hydrogen, hydroxyl, or a monovalent hydrocarbon group of 1 to 15 carbon atoms which may contain at least one hetero atom. Examples of the monovalent hydrocarbon group are the same as exemplified above for $R^2$ and $R^3$.

$R^5$ is an acid labile group. The acid labile group may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

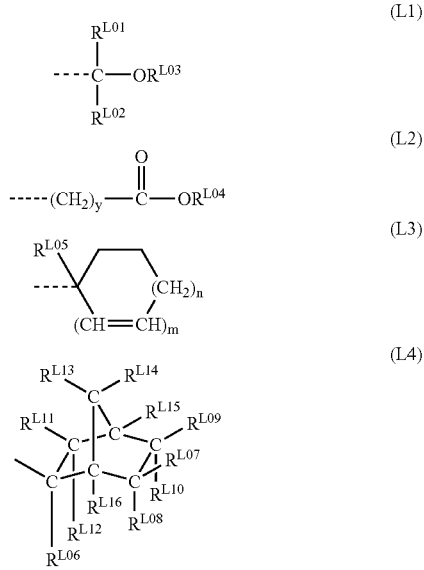

In these formulae and throughout the specification, a broken line denotes a valence bond. $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, and n-octyl. $R^{L03}$ is a monovalent hydrocarbon group of 1 to 18 carbon atoms, preferably 1 to 10 carbon atoms, which may contain at least one hetero atom such as oxygen, examples of which include unsubstituted straight, branched or cyclic alkyl groups and straight, branched or cyclic alkyl groups in which some hydrogen atoms are replaced by hydroxyl, alkoxy, oxo, amino, alkylamino or the like. Illustrative examples are the substituted alkyl groups shown below.

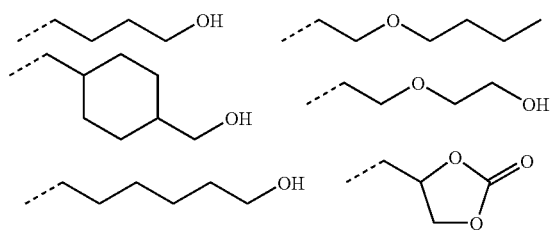

A pair of $R^{L01}$ and $R^{L02}$, $R^{L01}$ and $R^{L03}$, or $R^{L02}$ and $R^{L03}$ may bond together to form a ring. Each of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter y is an integer of 0 to 6.

$R^{L05}$ is a monovalent $C_1$-$C_8$ hydrocarbon group which may contain at least one hetero atom or a substituted or unsubstituted $C_6$-$C_{20}$ aryl group. Examples of the monovalent hydrocarbon group which may contain at least one hetero atom include straight, branched or cyclic alkyl groups such as methyl, ethyl, propyl, isopropyl, n-butyl, sec-butyl, tert-butyl, tert-amyl, n-pentyl, n-hexyl, cyclopentyl, and cyclohexyl, and substituted forms of the foregoing groups in which some hydrogen atoms are replaced by hydroxyl, alkoxy, carboxy, alkoxycarbonyl, oxo, amino, alkylamino, cyano, mercapto, alkylthio, sulfo or other groups. Exemplary aryl groups are phenyl, methylphenyl, naphthyl, anthryl, phenanthryl, and pyrenyl. Letter m is equal to 0 or 1, n is equal to 0, 1, 2 or 3, and 2 m+n is equal to 2 or 3.

$R^{L06}$ is a monovalent $C_1$-$C_8$ hydrocarbon group which may contain at least one hetero atom or a substituted or unsubstituted $C_6$-$C_{20}$ aryl group. Examples of these groups are the same as exemplified for $R^{L05}$.

$R^{L07}$ to $R^{L16}$ independently represent hydrogen or monovalent $C_1$-$C_{15}$ hydrocarbon groups which may contain at least one hetero atom. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing groups in which some hydrogen atoms are replaced by hydroxyl, alkoxy, carboxy, alkoxycarbonyl, oxo, amino, alkylamino, cyano, mercapto, alkylthio, sulfo or other groups. Alternatively, $R^{L07}$ to $R^{L16}$, taken together, form a ring (for example, a pair of $R^{L07}$ and $R^{L08}$, $R^{L07}$ and $R^{L09}$, $R^{L08}$ and $R^{L10}$, $R^{L09}$ and $R^{L10}$ $R^{L11}$ and $R^{L12}$ $R^{L13}$ and $R^{L14}$, or a similar pair form a ring). Each of $R^{L07}$ to $R^{L16}$ represents a divalent $C_1$-$C_{15}$ hydrocarbon group which may contain at least one hetero atom, when they form a ring, examples of which are the ones exemplified above for the monovalent hydrocarbon groups, with one hydrogen atom being eliminated. Two of $R^{L07}$ to $R^{L10}$ which are attached to adjoining carbon atoms (for example, a pair of $R^{L07}$ and $R^{L09}$, $R^{L09}$ and $R^{L15}$ $R^{L13}$ and $R^{L15}$ or a similar pair) may bond together directly to form a double bond.

Of the acid labile groups of formula (L1), the straight and branched ones are exemplified by the following groups.

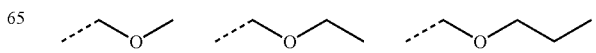

-continued

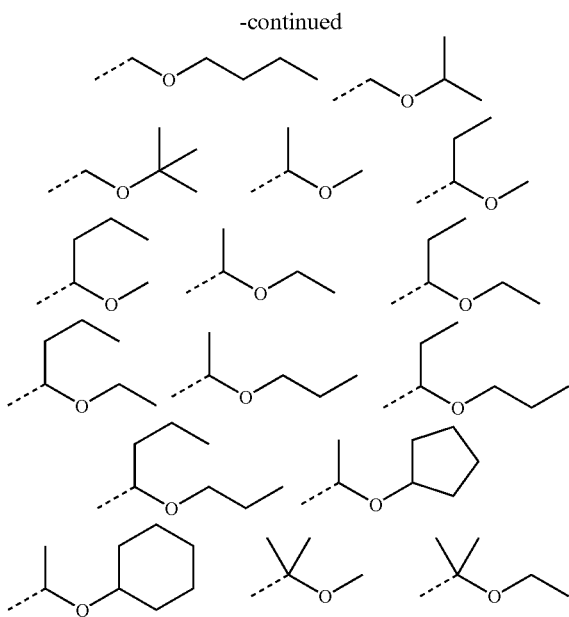

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Examples of the acid labile groups of formula (L4) include the following group. The broken line shows the bonding position and direction.

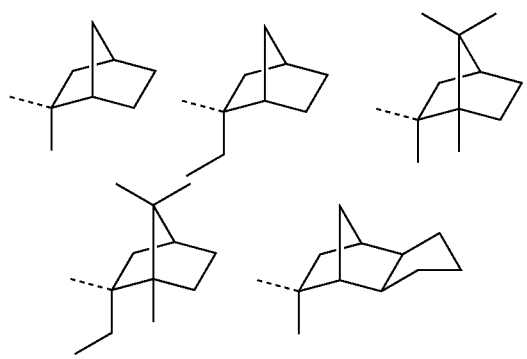

-continued

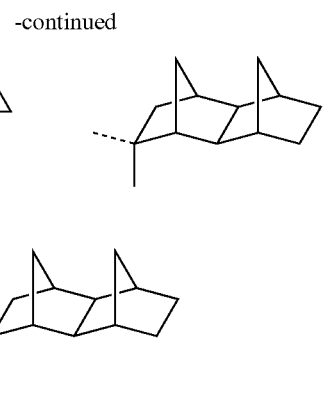

Examples of the tertiary $C_4$-$C_{20}$ alkyl groups, trialkylsilyl groups in which each alkyl moiety has 1 to 6 carbon atoms, and $C_4$-$C_{20}$ oxoalkyl groups are as exemplified for $R^{L04}$.

In formulae (1) and (2), $R^2$, $R^3$, $R^4$ and $R^5$ may be suitably selected in view of various properties (such as transparency, etching resistance and dissolution) of a resist resin resulting from polymerization of the polymerizable fluorinated ester compound.

Depending on the type of $R^2$, $R^3$, $R^4$ and $OR^5$, the carbon atom to which they are bonded can be an asymmetric carbon atom, which means the presence of enantiomers or diastereomers. The general formula (1) or (2) collectively represents all such stereoisomers. The stereoisomers may be used alone or as a mixture.

Illustrative, non-limiting examples of the polymerizable fluorinated ester compounds of the invention are given below. In the following formulae, Me is methyl, t-Bu is tert-butyl, and Ph is phenyl.

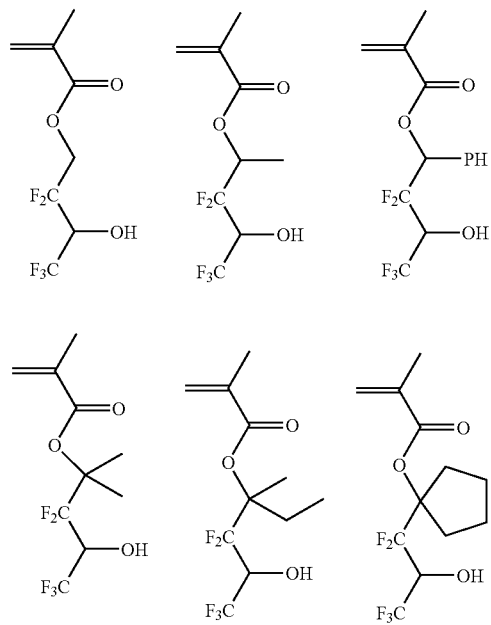

-continued
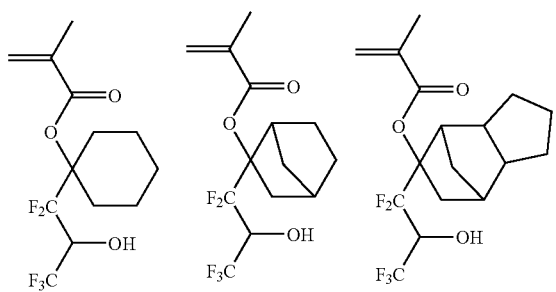
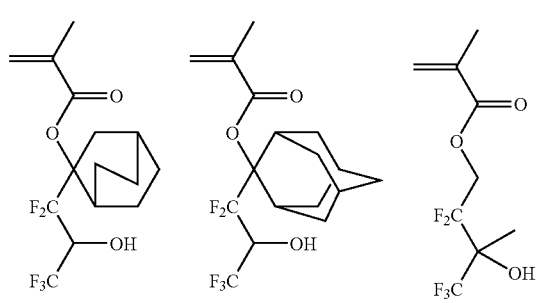
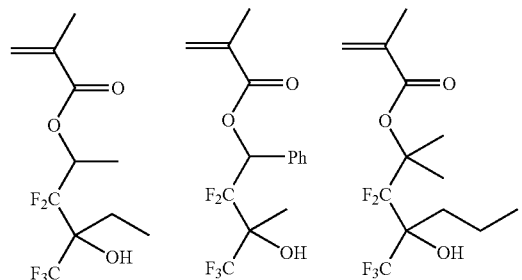
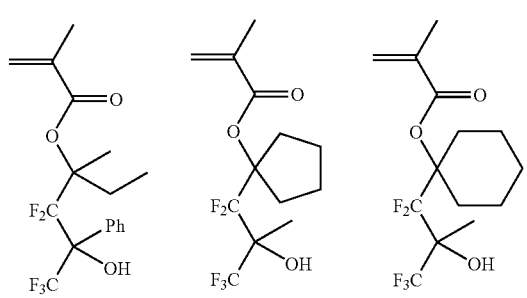
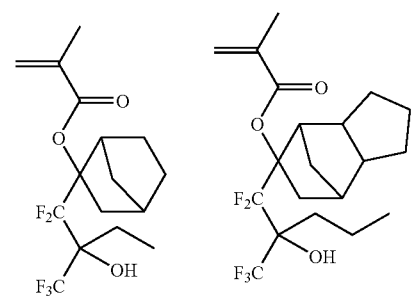
-continued
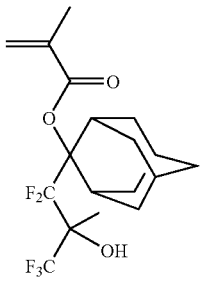
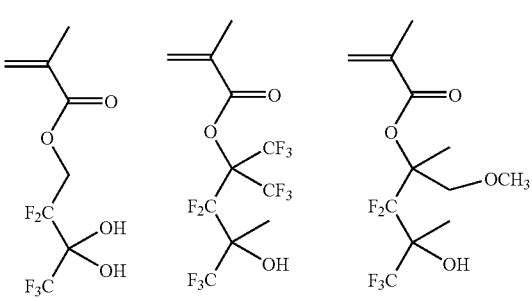
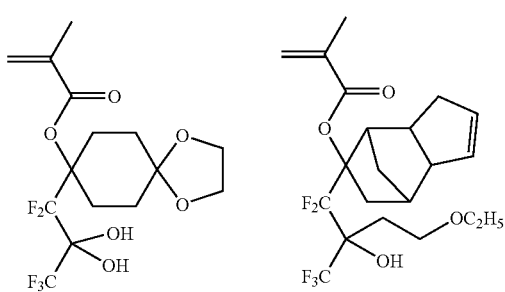
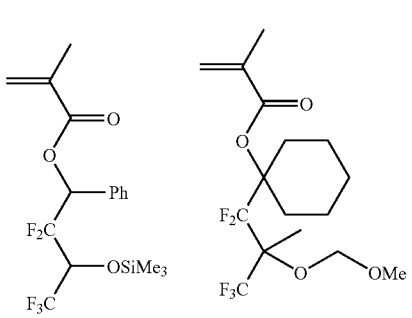
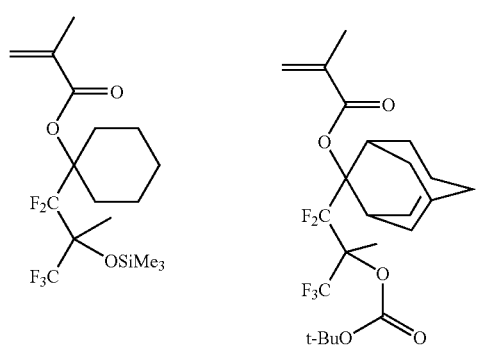

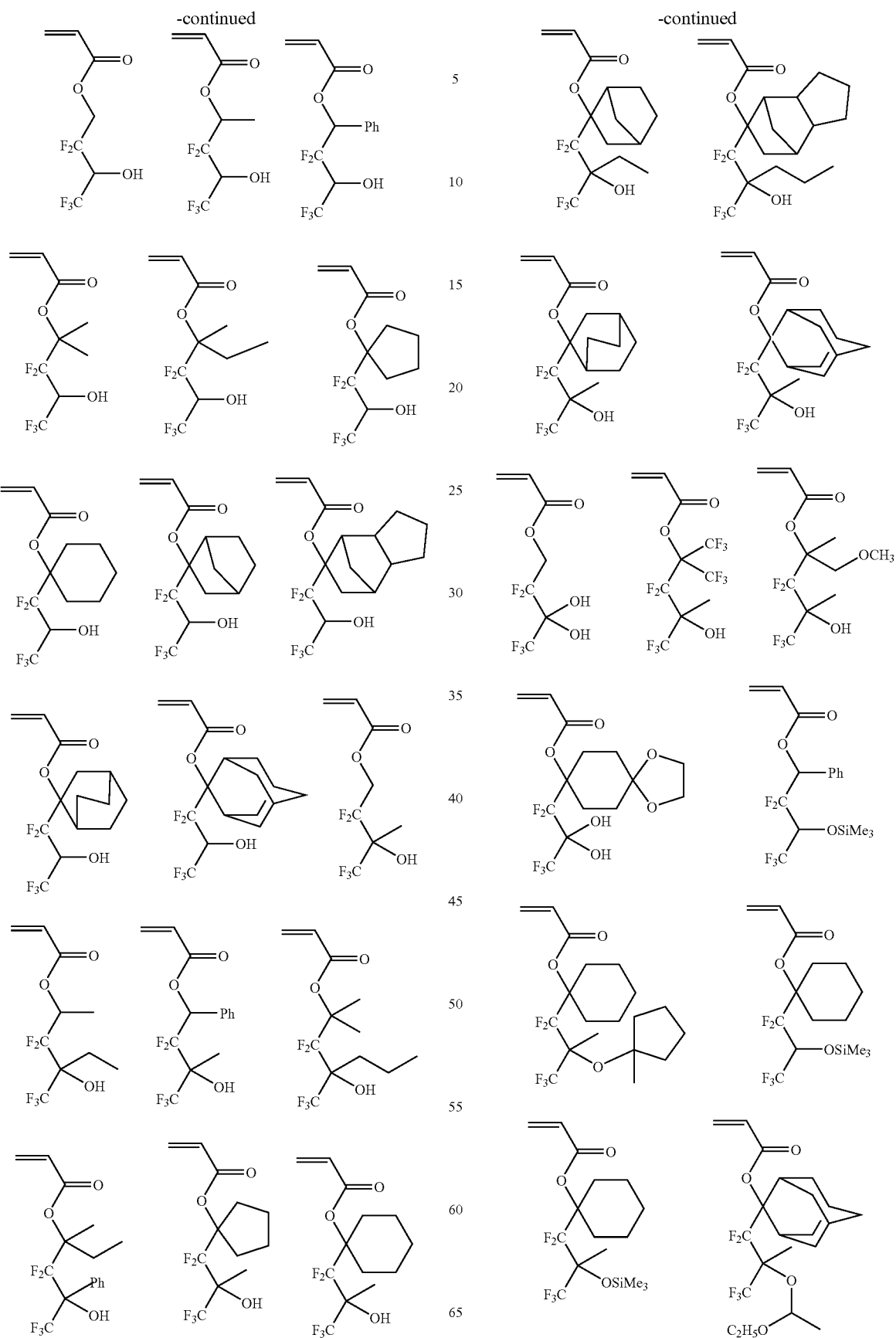

-continued

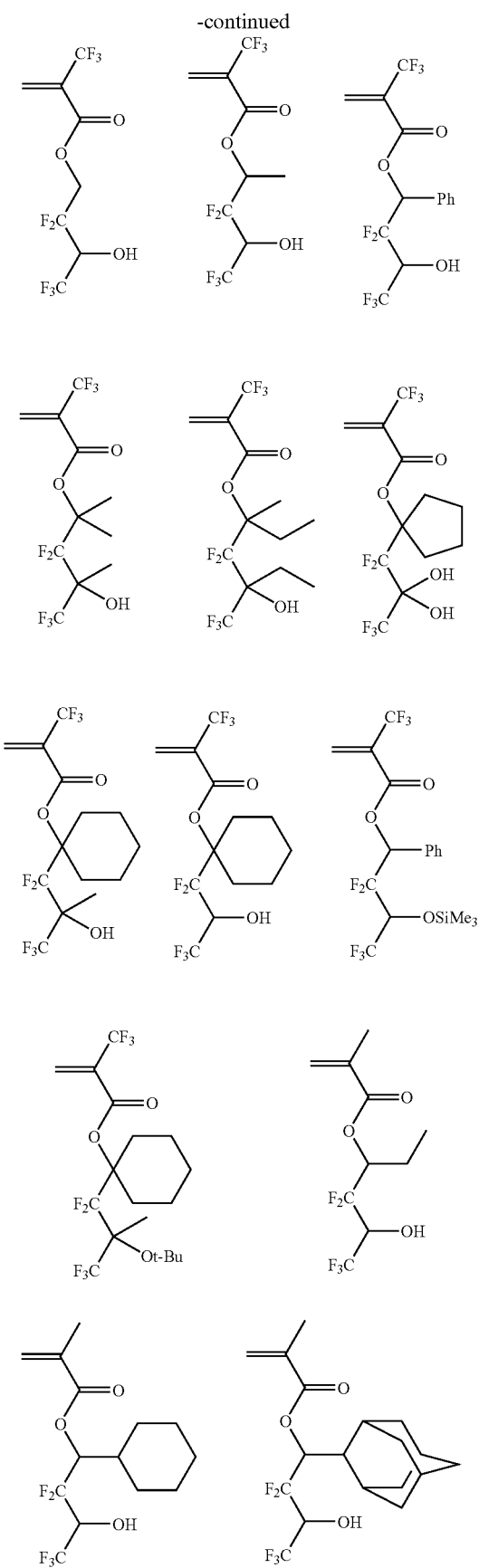

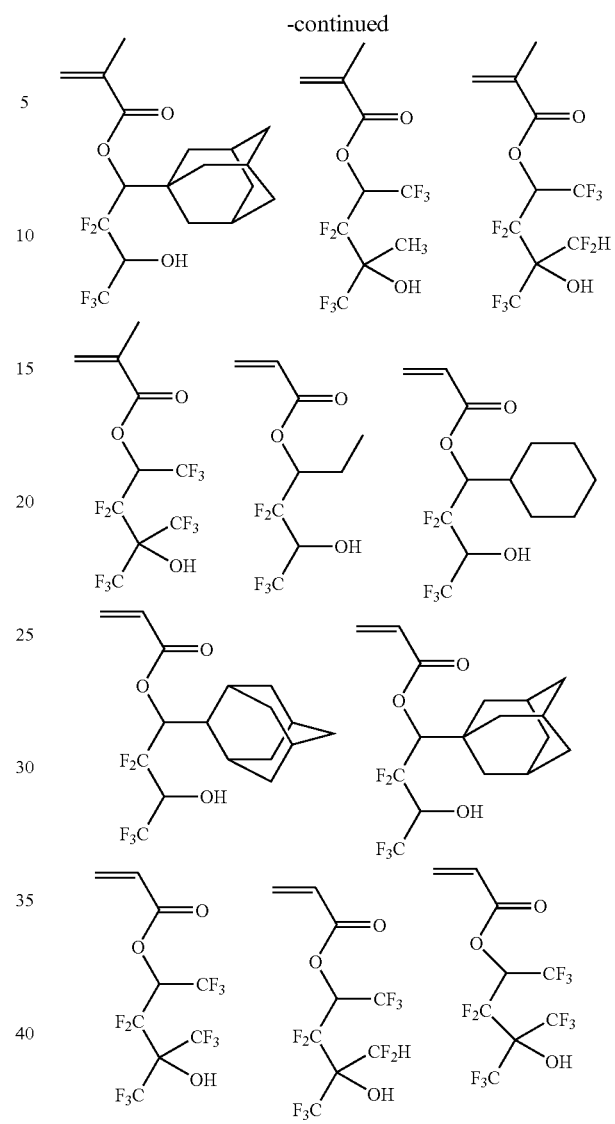

Next, processes of preparing the polymerizable fluorinated ester compounds of the invention are described.

The starting material is a ketoalcohol compound (3). It can be readily synthesized by reacting a carbonyl compound (8) with an enolate (1,1,3,3,3-pentafluoro-2-propenyl oxide) which is prepared from 1,1,1,3,3,3-hexafluoro-2-propanol (which is commercially available in bulk, liquid at room temperature due to a melting point of −4° C. to −2° C. and a boiling point of 59-60° C., and easy to handle). See T. Nakai et al., Tetrahedron Letters, Vol. 29, p. 4119, 1988 and T. Nakai et al., Organic Syntheses, Vol. 76, p. 151, 1998. In this nucleophilic addition reaction of fluoroenolate to carbonyl compound, various aldehydes and ketones may be used as the carbonyl compound (8).

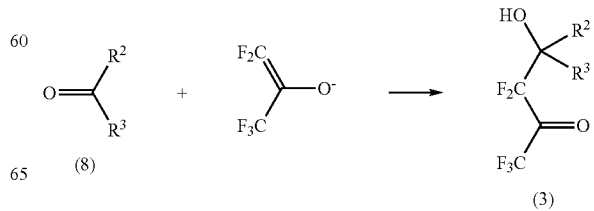

The ketoalcohol compound (3) thus produced is sometimes available in the form of a hydrate of the general formula (9) in which water is added to the carbonyl group, when subjected to work-up process using water, or an oxetane hemi-acetal compound of the general formula (10) in which the hydroxyl group is added intramolecularly to the carbonyl group, or a mixture of these three.

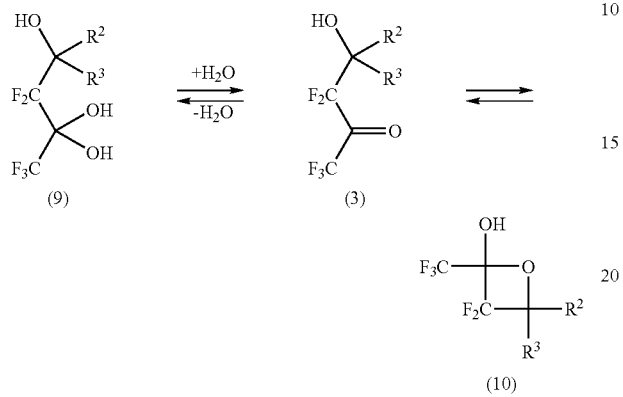

(9) (3)

(10)

Herein, such reaction products are collectively represented by the general formula (3) because in some cases, the mixture can be directly used in the subsequent reaction, and in some other cases, equilibrium can be biased toward the ketoalcohol compound by simple dehydrating operation, prior to the subsequent reaction.

In the event $R^2$ and $R^3$ are different, the carbon atom to which they are bonded becomes asymmetric carbon. In the oxetane hemi-acetal compound (10), the carbon atom to which $CF_3$ and hydroxyl groups are bonded becomes asymmetric carbon. This means the presence of enantiomers or diastereomers. The general formula (3) collectively represents all such stereoisomers. The stereoisomers may be used alone or as a mixture.

If this ketoalcohol compound (3) equivalent (equilibrium mixture) is directly acylated, there can be formed a product in which the hydroxyl group on the oxetane compound (10) is acylated, but not a keto ester compound in which the hydroxyl group on the compound (3) is acylated. For this reason, it is preferred that reaction with $R^4$—Z precede acylation.

A first process of preparing the polymerizable fluorinated ester compounds of the invention involves reacting a ketoalcohol compound having the general formula (3) with a compound of the general formula: $R^4$—Z to form a diol compound having the general formula (4), and acylating the diol compound to form a polymerizable fluorinated ester compound having the general formula (1).

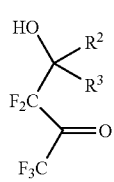

(3)

-continued

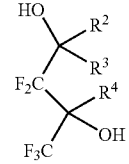

(4)

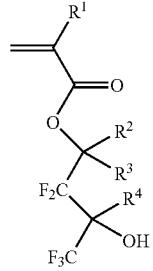

(1)

In the formulae, as previously defined, $R^1$ is hydrogen, methyl or trifluoromethyl, $R^2$ and $R^3$ are each independently hydrogen or a monovalent hydrocarbon group of 1 to 15 carbon atoms which may contain at least one hetero atom, a pair of $R^2$ and $R^3$ may bond together to form a ring, and if so, each of $R^2$ and $R^3$ is a divalent hydrocarbon group of 1 to 15 carbon atoms which may contain at least one hetero atom, $R^4$ is hydrogen, hydroxyl, or a monovalent hydrocarbon group of 1 to 15 carbon atoms which may contain at least one hetero atom, and Z is such a monovalent group that $R^4$—Z provides a $R^4$ anion equivalent.

In the first step, the starting reactant, ketoalcohol compound (3) is reacted with a compound $R^4$—Z.

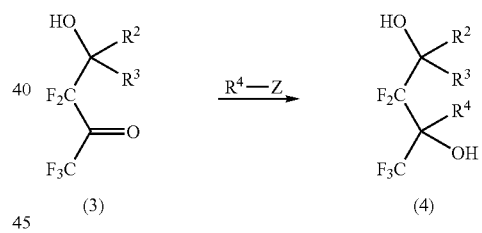

(3) (4)

This reaction is performed by combining the compound (3) with $R^4$—Z in a solvent or without solvent. $R^4$—Z represents a $R^4$ anion equivalent and is suitably selected depending on the desired type of $R^4$. Examples of $R^4$—Z include water (wherein $R^4$ is hydroxyl), alkyl metals (wherein $R^4$ is a hydrocarbon group) such as methyllithium, butyllithium, phenyllithium, methylmagnesium chloride, ethylmagnesium chloride, and phenylmagnesium chloride, metal hydrides (wherein $R^4$ is a hydrogen atom) such as sodium hydride, potassium hydride, calcium hydride, aluminum hydride, borane, and diisobutylaluminum hydride, and metal hydrogen complexes or alkyl and alkoxy derivatives thereof (wherein $R^4$ is a hydrogen atom) such as sodium borohydride and lithium aluminum hydride. An appropriate amount of $R^4$—Z used is from 1 mole to a large excess per mole of the compound (3). A more appropriate amount of $R^4$—Z is from 2 moles to a large excess per mole of the compound (3) because free hydroxyl group is present in the ketoalcohol compound (3) as the reaction substrate.

When the reaction is performed in a solvent, the solvent used is selected from among hydrocarbons such as hexane, heptane, benzene, toluene, xylene and cumene, ethers such as dibutyl ether, diethylene glycol diethyl ether, diethylene glycol dimethyl ether, tetrahydrofuran and 1,4-dioxane, nitriles such as acetonitrile, ketones such as acetone, esters such as ethyl acetate, and aprotic polar solvents such as N,N-dimethylformamide and hexamethylphosphoric triamide, alone or as mixtures of any.

For the addition reaction, an appropriate reaction temperature may be selected depending on the type of $R^4$—Z. The reaction temperature is typically from −50° C. to approximately the boiling point of the solvent, preferably from −20° C. to 100° C. It is desired for higher yields that the reaction time is determined by monitoring the progress of reaction by gas chromatography (GC) or thin-layer chromatography (TLC). The reaction time is usually about 0.1 hour to about 50 hours. After the completion of reaction, the target diol compound (4) is separated from the reaction mixture by a conventional aqueous work-up procedure. If necessary, the compound (4) can be purified by any conventional technique such as recrystallization, chromatography or distillation.

The second step is to acylate the diol compound (4). In this step, the regio-selectivity of reaction is a issue since the diol compound (4) has two hydroxyl groups which can be potentially acylated. That is, there can be produced the target compound (1) and a regioisomer having the general formula (1').

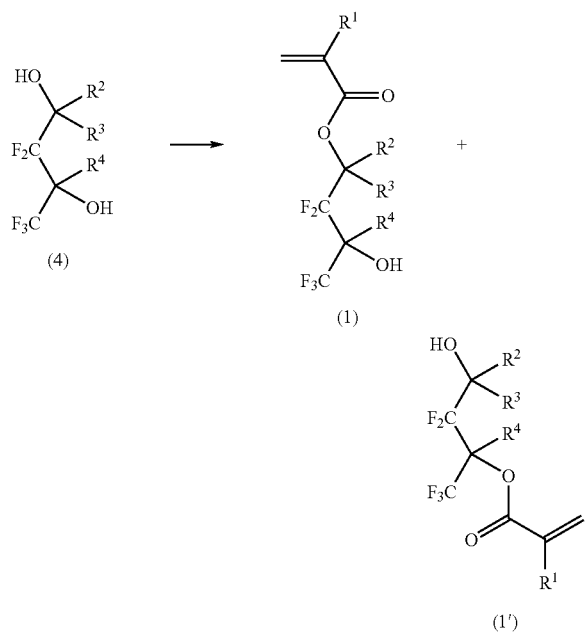

The compound (1) is selectively obtained in some cases, for example, when the two hydroxyl groups on the diol compound (4) are distinguished by steric hindrance so that the desired position to be acylated is sterically less hindered, or when reaction conditions are properly controlled because the two hydroxyl groups have different acidity despite an approximately equal extent of steric hindrance. In these cases, the diol compound (4) can be used as the reaction substrate without any manipulation, i.e., without protecting any hydroxyl group, and subjected to acylation reaction to be described later. This process is of great commercial worth due to shorter or fewer steps involved, as compared with the process requiring protecting and deprotecting steps to be described later.

For the acylation reaction, conventional esterification methods, such as reaction with acylating agents, reaction with carboxylic acids and transesterification are applicable.

In the reaction using acylating agents, the diol compound (4), an acylating agent and a base are sequentially or simultaneously mixed, preferably in a solvent where reaction takes place. Examples of the solvent used herein include chlorinated solvents such as methylene chloride, chloroform and trichloroethylene, hydrocarbons such as hexane, heptane, benzene, toluene, xylene and cumene, ethers such as dibutyl ether, diethylene glycol diethyl ether diethylene glycol dimethyl ether, tetrahydrofuran, and 1,4-dioxane, nitriles such as acetonitrile, ketones such as acetone and 2-butanone, esters such as ethyl acetate and n-butyl acetate, and aprotic polar solvents such as N,N-dimethylformamide, dimethyl sulfoxide, and hexamethylphosphoric triamide, alone or as mixtures of any. Examples of the acylating agent include acid halides such as acryloyl chloride, methacryloyl chloride, acryloyl bromide, methacryloyl bromide, and α-trifluoromethylacryloyl chloride, and acid anhydrides such as acrylic anhydride, methacrylic anhydride, α-trifluoromethylacrylic anhydride, acrylic acid/trifluoroacetic acid mixed anhydride, methacrylic acid/trifluoroacetic acid mixed anhydride, α-trifluoromethylacrylic acid/trifluoroacetic acid mixed anhydride, acrylic acid/p-nitrobenzoic acid mixed anhydride, methacrylic acid/p-nitrobenzoic acid mixed anhydride, acrylic acid/ethylcarbonic acid mixed anhydride, and methacrylic acid/ethylcarbonic acid mixed anhydride. Examples of the base include triethylamine, diisopropylethylamine, N,N-dimethylaniline, pyridine, and 4-dimethylaminopyridine. An appropriate reaction temperature may be selected depending on the type of acylating agent used and other reaction conditions. The reaction temperature is typically from −50° C. to approximately the boiling point of the solvent, preferably from −20° C. to room temperature. An appropriate amount of the acylating agent used is from 1 to 40 moles, more preferably 1 to 5 moles per mole of the diol compound (4), though it depends on the structure of the agent.

In the course of reaction using the acylating agent, a regioisomer (1') may form as a main product at the initial phase of reaction, and as the reaction continues longer, gradual isomerization into the target compound (1) may take place. It accounts for this phenomenon that under basic conditions, the hydroxyl group having a higher acidity (susceptible to deprotonation by base) is acylated at the initial phase so that the regioisomer (1') is likely to form as a kinetic product, but the target compound (1) which is believed to be more stable in the system as a thermodynamic product accumulates over a long term of reaction.

The reaction with carboxylic acids is a dehydrating reaction from a corresponding carboxylic acid, i.e., any of acrylic acid, methacrylic acid and α-trifluoromethylacrylic acid and the reactant, diol compound (4), which is generally performed in the presence of an acid catalyst. An appropriate amount of carboxylic acid used is 1 to 40 moles, more preferably 1 to 5 moles per mole of the diol compound (4), though it depends on the structure of acid. Examples of the acid catalyst include inorganic acids such as hydrochloric acid, hydrobromic acid, sulfuric acid, and nitric acid, and organic acids such as oxalic acid, trifluoroacetic acid, methanesulfonic acid, benzenesulfonic acid, and p-toluenesulfonic acid, alone or as mixtures of any. An appropriate amount of the acid catalyst used is 0.001 to 1 mole, more preferably 0.01 to 0.05 mole per mole of the diol compound (4). Examples of the solvent used are as exemplified above for the reaction with the acylating agent. The reaction temperature is preferably from −50° C. to approximately the boiling point of the solvent. The reaction may also be performed in a solvent comprising a hydrocarbon such as hexane, heptane, benzene, toluene, xylene or cumene, removing water formed out of the system by azeotropy. In this embodiment, the water may be distilled off heating the solvent under reflux at the boiling point in atmospheric pressure, or the water be distilled off under reduced pressure at a lower temperature than the boiling point.

The transesterification is implemented by reacting the reactant, diol compound (4) with a corresponding carboxylic acid ester, i.e., any of acrylate, methacrylate and α-trifluoromethylacrylate in the presence of a catalyst and removing the alcohol formed. The carboxylic acid esters used are preferably primary alkyl esters. Inter alia, methyl, ethyl and n-propyl esters are preferred because of low cost and ease of reaction progress. An appropriate amount of carboxylic acid ester used is 1 to 40 moles, more preferably 1 to 5 moles per mole of the diol compound (4), though it depends on the structure of ester. Examples of the catalyst include inorganic acids such as hydrochloric acid, hydrobromic acid, sulfuric acid, and nitric acid, organic acids such as oxalic acid, trifluoroacetic acid, methanesulfonic acid, benzenesulfonic acid, and p-toluenesulfonic acid, bases such as sodium methoxide, sodium ethoxide, potassium t-butoxide, and 4-dimethylaminopyridine, and salts such as sodium cyamide, potassium cyamide, sodium acetate, potassium acetate, calcium acetate, tin acetate, aluminum acetate, aluminum acetoacetate, alumina, and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide, alone or as mixtures of any. An appropriate amount of the catalyst used is 0.001 to 20 moles, more preferably 0.01 to 0.05 mole per mole of the diol compound (4). The reaction may be performed in a solventless system (the reagent, carboxylic acid ester itself may serve as a solvent), which is preferred in that extra operations such as concentration and solvent recovery are eliminated. A solvent may be used in a supplemental manner for the purpose of preventing polymerization of the target compound and reagent. Examples of the solvent, if used, include hydrocarbons such as hexane, heptane, benzene, toluene, xylene and cumene, and ethers such as dibutyl ether, diethylene glycol diethyl ether, diethylene glycol dimethyl ether, tetrahydrofuran, and 1,4-dioxane, alone or in admixture. An appropriate reaction temperature may be selected depending on the type of carboxylic acid ester used and other reaction conditions. Usually, the reaction is performed at elevated temperature. Better results are obtained when the reaction is performed at a temperature approximate to the boiling point of a low boiling point alcohol formed by transesterification reaction such as methanol, ethanol or 1-propanol, whereby the alcohol formed is distilled off during the reaction. The alcohol may be distilled off at a lower temperature than the boiling point under reduced pressure.

It is desired for higher yields that the time of acylating reaction is determined by monitoring the progress of reaction (including not only acylating reaction, but also isomerization) by GC or TLC. The reaction time is usually about 0.1 hour to about 240 hours. After the completion of reaction, the target fluorinated ester compound (1) is isolated from the reaction mixture by a conventional work-up such as aqueous work-up or concentration.

If necessary, the compound (1) can be purified by any conventional technique such as recrystallization, chromatography or distillation. The target compound (1) and its regioisomer (1') may be separated by such a purifying technique. Alternatively, a mixture of compounds (1) and (1') may be used in the subsequent step like the manufacture of resin. The molar ratio of isomers (1) and (1') may have any arbitrary value from 0 to 1 although the molar ratio of compound (1) having a phenol-like acidity should preferably be at least 0.3, more preferably at least 0.5.

The reaction intermediate (4) and the target compound (1) have a possibility that depending on the type of $R^2$, $R^3$ and $R^4$, the carbon atoms to which they are bonded become asymmetric carbons, which means the presence of enantiomers or diastereomers. The general formula (4) or (1) collectively represents all such stereoisomers. The stereoisomers may be used alone or as a mixture.

A second process for preparing the polymerizable fluorinated ester compounds of the invention comprises the steps of reacting a ketoalcohol compound having the general formula (3) with a compound of the general formula: $R^4$—Z to form a diol compound having the general formula (4), protecting one of the hydroxyl groups of the diol compound so as to form an alcohol compound having the general formula (5), acylating the alcohol compound to form a protected polymerizable fluorinated ester compound having the general formula (6), and deprotecting the compound of formula (6) into a polymerizable fluorinated ester compound having the general formula (1). The second process is advantageously employed when the first process, that is, direct acylating reaction of diol compound (4) is less regioselective.

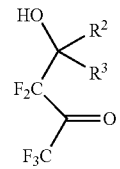

(3)

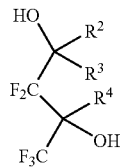

(4)

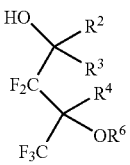

(5)

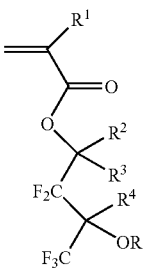

(6)

-continued

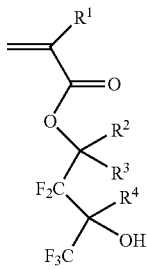

(1)

Herein, $R^1$ to $R^4$, Z and $R^4$—Z are as defined above, $R^6$ is a protective group.

For the step of reacting a ketoalcohol compound (3) with a compound: $R^4$—Z to form a diol compound (4), the same as described for the first process is applicable. For the step of acylating the protected alcohol compound (5) to form a protected polymerizable fluorinated ester compound (6), the same as described for the first process, direct acylating reaction of diol compound (4) to form polymerizable fluorinated ester compound (1) is applicable. In this step of the second process, since the protected alcohol compound (5) has only one hydroxyl group subject to acylation, reagents including acylating agent, carboxylic acid, and ester may be used in increased equivalent amounts to accelerate the reaction.

The protective group $R^6$ includes those groups exemplified above for the acid labile group $R^5$ and other protective groups.

When the protective group $R^6$ is the acid labile group $R^5$, the protected polymerizable fluorinated ester compound (6) is identical with the polymerizable fluorinated ester compound protected with acid labile group represented by formula (2). Then the process is a process of preparing polymerizable fluorinated ester compounds (2).

Examples of the other protective group include acyl groups such as formyl, benzoylformyl, acetyl, chloroacetyl, dichloroacetyl, trichloroacetyl, trifluoroacetyl, methoxyacetyl, triphenylmethoxyacetyl, phenoxyacetyl, phenylacetyl, nicotinyl, 3-phenylpropionyl, 4-pentenoyl, 4-oxopentanoyl, pyvaloyl, 1-adamantoyl, crotonyl, 4-methoxycrotonyl, benzoyl, 4-phenylbenzoyl, and mesytoyl.

The protecting and deprotecting reactions of hydroxyl group widely vary with the type of $R^6$ and may be performed in a conventional manner. In an example where the hydroxyl group is protected with an acyl group, conventional esterification methods may be used. The above-described reaction with acylating agent, reaction with carboxylic acid and transesterification are applicable using corresponding reagents. For deprotection of acyl group, hydrolysis/solvolysis reaction using acids or bases, and deprotecting reaction under acidic conditions may be employed although the deprotecting reaction is not limited thereto.

If necessary, the reaction intermediates (4), (5), (6) and target compounds (1) and (2) (corresponding to compound (6) wherein the protective group $R^6$ is an acid labile group $R^5$) can be purified by any conventional technique such as recrystallization, chromatography or distillation. The reaction intermediates (4), (5), (6) and the target compounds (1) and (2) have a possibility that depending on the type of $R^2$, $R^3$, $R^4$ and $OR^5$, the carbon atom to which they are bonded becomes asymmetric carbon, which means the presence of enantiomers or diastereomers. The general formula (1) or (2) collectively represents all such stereoisomers. The stereoisomers may be used alone or as a mixture.

A third process for preparing the polymerizable fluorinated ester compounds of the invention comprises the step of protecting a polymerizable fluorinated ester compound having the general formula (1) with an acid labile group to form a polymerizable fluorinated ester compound having the general formula (2).

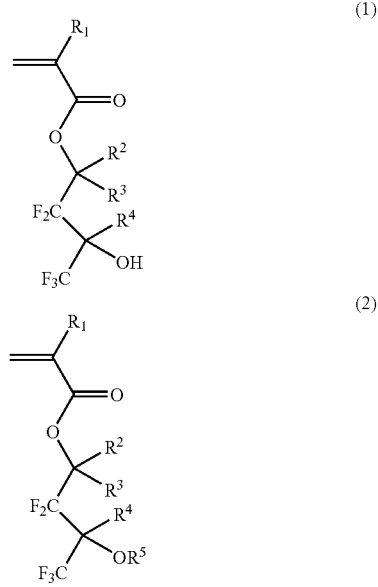

Herein, $R^1$ to $R^5$ are as defined above.

The third process is through protection of the target compound (1) with an acid labile group to form the target compound protected with an acid labile group (2). The type of acid labile group used herein is the same as described above. The protection reaction may be performed by conventional methods. In an example where the hydroxyl group is protected with an acyl group, conventional esterification methods may be used. The above-described reaction with acylating agent, reaction with carboxylic acid and transesterification are applicable using corresponding reagents. In another example where an ether group is used for protection, reaction with halides under basic conditions, and addition reaction to unsaturated compounds under acidic conditions are applicable. In a further example of silyl protection, reaction with chlorosilane under basic conditions is applicable. The protection reaction is not limited to the foregoing.

If necessary, the target compound (2) can be purified by any conventional technique such as recrystallization, chromatography or distillation. The target compound (2) has a possibility that depending on the type of $R^2$, $R^3$, $R^4$ and $OR^5$, the carbon atoms to which they are bonded become asymmetric carbons, which means the presence of enantiomers or diastereomers. The general formula (2) collectively represents all such stereoisomers. The stereoisomers may be used alone or as a mixture.

Using the polymerizable fluorinated ester compounds of the invention, homopolymers may be prepared by common techniques like radical polymerization. Alternatively, copolymers may be prepared by copolymerization with at least one type of other polymerizable monomer.

Polymers obtained through the polymerization of polymerizable fluorinated ester compounds according to the invention are fully transparent to radiation having a wavelength of up to 500 nm, especially up to 200 nm, and have good development properties due to the presence of phenol-like acidic hydroxyl groups, when used as the base resin in radiation-sensitive resist compositions. Examples of the radiation having a wavelength of up to 200 nm include ArF laser light (193 nm), $F_2$ laser light (157 nm), $Ar_2$ laser light (126 nm), and extreme ultraviolet radiation (EUV 13 nm).

EXAMPLE

Examples of the invention are given below by way of illustration and not by way of limitation.

Example 1

Synthesis of 2-(2-hydroxy-2-methyl-1,1,3,3,3-pentafluoro-propyl)-2-adamantyl methacrylate

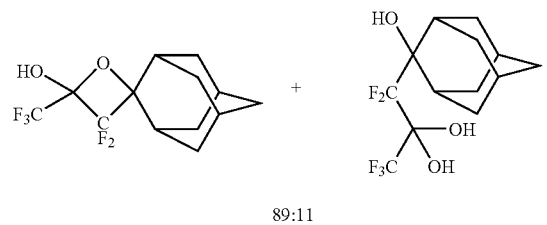

89:11 colorless solid

IR (KBr): ν=3588, 3442, 2921, 2865, 1456, 1338, 1203, 1041, 912 cm$^{-1}$ $^1$H-NMR (600 MHz in DMSO-d6): δ=1.46-2.41 (14H, m), 6.97 (0.11H, s, adamantyl-OH), 8.11 (2×0.11H, s, two hydroxyl groups of hydrate), 9.44 (0.89H, s, oxetane-OH) ppm $^{19}$F-NMR (565 MHz in DMSO-d6, trifluoroacetic acid standard): δ=−125.6 (0.89F, dq, J=208, 13 Hz), −122.5

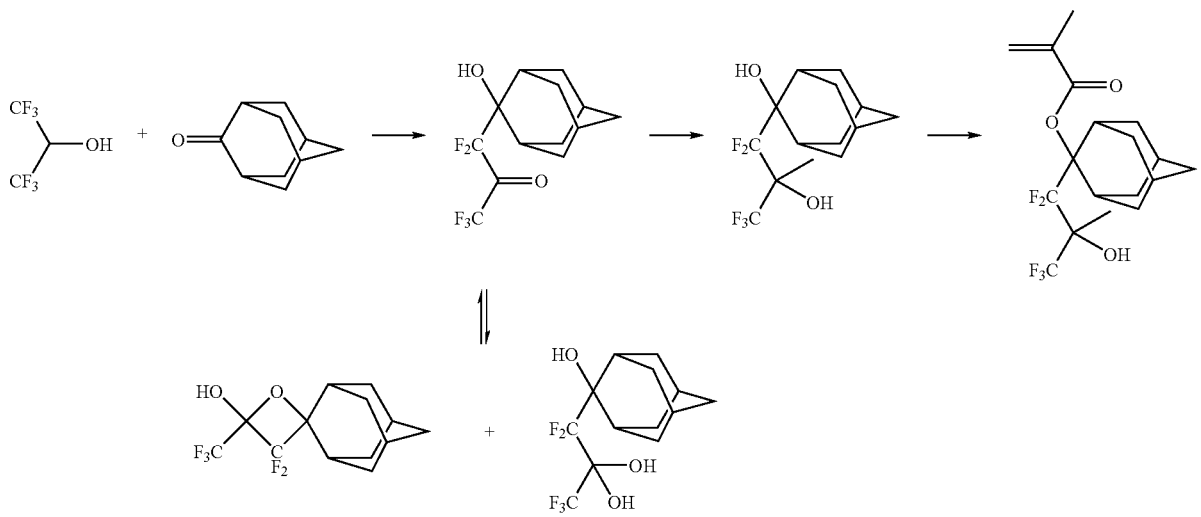

<1-1> Synthesis of 2-(2-oxo-1,1,3,3,3-pentafluoropropyl)-adamantan-2-ol equivalent With stirring under nitrogen atmosphere, a mixture of 41.5 g of 1,1,1,3,3,3-hexafluoro-2-propanol and 500 ml of tetrahydrofuran was cooled to −50° C. To the mixture, 200 ml of 2.46M n-butyllithium in n-hexane was added dropwise. The mixture was stirred at −70° C. for 10 minutes and then at 5° C. for 90 minutes. To the reaction mixture, 18.5 g of 2-adamantane in 100 ml of tetrahydrofuran was added. The mixture was stirred at 5° C. for 1 hour and then at room temperature for 18 hours. The reaction mixture was mixed 400 ml of 10% hydrochloric acid and extracted with ethyl acetate. Through conventional work-up procedure including washing, drying and concentration, there was obtained as a crude product, 36.9 g (quantitative yield) of a mixture of an oxetane hemi-acetal compound, and a hydrate which is an equivalent of the target ketoalcohol compound, in a ratio of about 89:11.

A mixture of spiro[adamantane-2,2'-(3',3'-difluoro-4'-hydroxy-4'-trifluoromethyloxetane)] and 2-(2,2-dihydroxy-1,1,3,3,3-pentafluoropropyl)adamantan-2-ol in a molar ratio of about 89:11.

(0.89F, d, J=208 Hz), −114.2 (2×0.11F, q, J=13 Hz), −81.7 (3×0.89F, d, J=13 Hz), −81.1 (3×0.11F, t, J=13 Hz) ppm <1-2> Synthesis of 2-(2-hydroxy-2-methyl-1,1,3,3,3-pentafluoropropyl)-adamantan-2-ol In 800 ml of benzene was dissolved 30 g of the crude product of ketoalcohol compound equivalent obtained in <1-1>. The solution was stirred and heated under reflux while the water formed was continuously removed. With stirring, the solution was added dropwise to 250 ml of a tetrahydrofuran solution of 1.0M methylmagnesium chloride. The mixture was stirred for 30 minutes at room temperature and then heated under reflux for one hours. After cooling, the reaction mixture was mixed with 700 ml of 10% hydrochloric acid and extracted with ethyl acetate. Through conventional work-up procedure including washing, drying and concentration, a crude product was obtained. Recrystallization from n-hexane gave 28.9 g (yield 92%) of the target diol compound.

2-(2-hydroxy-2-methyl-1,1,3,3,3-pentafluoropropyl)-adamantan-2-ol colorless solid IR (KBr): ν=3355, 3129, 2937, 2921, 2871, 1457, 1292, 1213, 1174, 1074, 1039 cm$^{-1}$ $^1$H-NMR (600 MHz in DMSO-d6): δ=1.39-1.46 (2H, t-like m), 1.55 (3H, br. s), 1.58-1.73 (5H, m), 1.79 (1H, br. s), 2.12-2.20 (3H, m), 2.22-2.30 (2H, t-like m), 2.33 (1H, br. s), 5.34 (1H, s, OH), 6.77 (1H, s, OH) ppm $^{13}$C-NMR (150 MHz in CDCl$_3$): δ=19.73, 26.60, 27.11, 32.94, 33.21, 33.57, 34.01, 34.09, 34.25, 39.03, 77.51 (t-like, J=24 Hz), 77.10-78.2 (m), 123.22 (dd-like, J=260, 267 Hz), 125.60 (q, J=289 Hz) ppm $^{19}$F-NMR (565 MHz in DMSO-d6, trifluoroacetic acid standard): δ=−110.5 (1F, d-like, J=262 Hz), −107.8 (1F, dq, J=262, 15 Hz), −77.0 (3F, t, J=15 Hz) ppm <1-3> Synthesis of 2-(2-hydroxy-2-methyl-1,1,3,3,3-pentafluoropropyl)-2-adamantyl methacrylate With stirring at 5° C., 14 ml of triethylamine was added dropwise to a mixture of 20 g of the diol compound obtained in <1-2>, 7.4 ml of methacryloyl chloride, and 500 ml of methylene chloride. The reaction mixture was stirred at 0° C. for 30 minutes and then at room temperature for 48 hours. The reaction was monitored by gas chromatography, finding a higher proportion of a regioisomer at the initial (target compound:regioisomer=24:76 after 4 hours), subsequent gradual isomerization into the target compound, and substantial conversion to the target compound after 48 hours. The reaction mixture was mixed with 100 ml of water, stirred at room temperature for 2 hours, and extracted with diethyl ether. Through conventional work-up procedure including washing, drying and concentration, a crude product was obtained. Recrystallization from n-hexane gave 20.7 g (yield 85%) of the target fluorinated ester compound.

2-(2-hydroxy-2-methyl-1,1,3,3,3-pentafluoropropyl)-2-adamantyl methacrylate colorless solid GC-MS (EI): (m/z)$^+$=41, 69, 141, 183, 207, 296, 382 (M$^+$)
GC-MS (CI, isobutane): (m/z)$^+$=277, 297, 383 [(M+H)$^+$]
IR (KBr): ν=3494, 2981, 2954, 2927, 2892, 2869, 1710, 1463, 1326, 1286, 1214, 1187, 1170, 1095, 1079, 1045 cm$^{-1}$ $^1$H-NMR (600 MHz in DMSO-d6): δ=1.50-1.88 (11H, m), 1.91 (3H, s), 2.02-2.32 (4H, m), 2.69 (1H, br. s), 3.41 (1H, br. s), 5.71 (1H, br. s), 6.04 (1H, br. s), 7.08 (1H, s) ppm $^{19}$F-NMR (565 MHz in DMSO-d6, trifluoroacetic acid standard): δ=−107.6 (1F, dd, J=277, 1790 Hz), −101.0 (1F, dd-like, J=277, 513 Hz), −76.5 (3F, d, J=275 Hz) ppm Comparative Example 1

Synthesis of spiro[adamantane-2,2'-(3',3'-difluoro-4'-trifluoromethyloxetan)]-4'-yl methacrylate by direct esterification of ketoalcohol compound equivalent

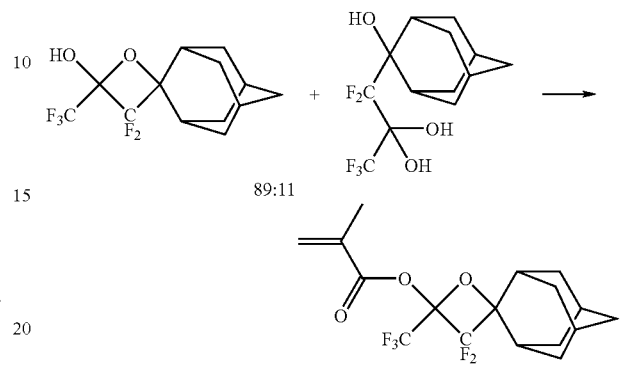

Esterification (methacryloylation) reaction was carried out as in <1-3> in Example 1, aside from using 5.0 g of a crude product of the ketoalcohol compound equivalent obtained in <1-1> instead of the diol compound obtained in <1-2>. The resulting product consisted of 5.5 g (yield 95%) of an ester of the above-identified oxetane compound, with no ester of hydrate being produced. It is thus believed that the reaction proceeded while the equilibrium was biased toward the oxetane compound.

spiro[adamantane-2,2'-(3',3'-difluoro-4'-trifluoromethyloxetan)]-4'-yl methacrylate colorless liquid IR (KBr): ν=2937, 2863, 1758, 1456, 1334, 1305, 1214, 1126, 1097, 1037, 968 cm$^{-1}$ $^1$H-NMR (600 MHz in DMSO-d6): δ=1.60-1.98 (15H, m), 2.30-2.33 (2H, m), 5.97 (1H, t, J=1 Hz), 6.19 (br. s) ppm $^{13}$C-NMR (150 MHz in DMSO-d6): δ=18.11, 25.54, 26.08, 31.66, 31.76, 31.87, 33.39 (d-like, J=4 Hz), 34.78, 35.00, 35.89, 99.86 (t, J=22 Hz), 101.5-103.5 (m), 116.65 (dd, J=282, 296 Hz), 120.13 (q, J=287 Hz), 130.21, 134.64, 162.22 ppm $^{19}$F-NMR (565 MHz in DMSO-d6, trifluoroacetic acid standard): δ=−123.36 (1F, dq, J=208, 13 Hz), −116.70 (1F, d, J=208 Hz), −76.36 (3F, d, J=13 Hz) ppm Example 2

Synthesis of 1-(2-hydroxy-1,1,3,3,3-pentafluoropropyl)-1-cyclohexyl methacrylate

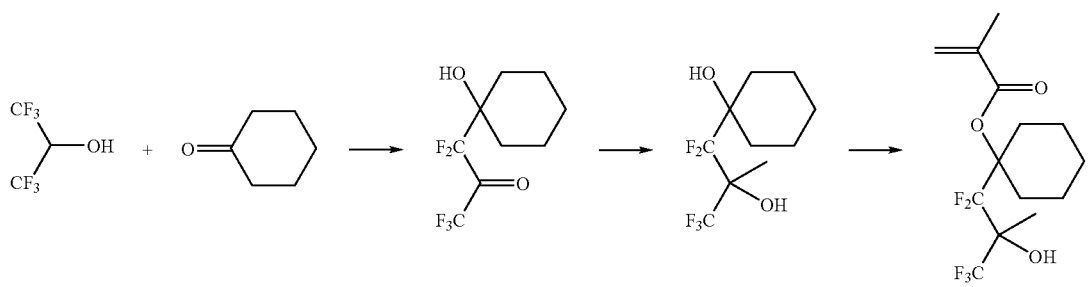

-continued

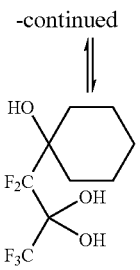

<2-1> Synthesis of 1-(2-oxo-1,1,3,3,3-pentafluoropropyl)-cyclohexan-1-ol equivalent Reaction was performed as in <1-1> of Example 1 aside from using 294 g of cyclohexanone instead of the 2-adamantanone in <1-1>. A crude product was obtained. Recrystallization from n-hexane gave 565 g (yield 71%) of a hydrate which was an equivalent of the target ketoalcohol compound.

1-(2,2-dihydroxy-1,1,3,3,3-pentafluoropropyl)cyclohexan-1-ol colorless solid

IR (KBr): ν=3505, 3353, 2954, 2865, 1452, 1307, 1205, 1103, 1076, 1062, 979 cm$^{-1}$ $^1$H-NMR (600 MHz in DMSO-d6): δ=1.12-1.20 (1H, m), 1.50-1.64 (7H, m), 1.97-2.05 (2H, m), 6.39 (1H, br. s, OH), 7.93 (2H, br. s, 2OH) ppm $^{13}$C-NMR (150 MHz in DMSO-d6): δ=21.67, 26.26, 31.29, 77.32 (t, J=25 Hz), 95.40 (hex, J=30 Hz), 118.84 (t, J=262 Hz), 123.63 (q, 292 Hz) ppm $^{19}$F-NMR (565 MHz in DMSO-d6, trifluoroacetic acid standard): δ=−123.8 (2F, q, J=13 Hz), −81.1 (3F, t, J=13 Hz) ppm <2-2> Synthesis of 1-(2-hydroxy-2-methyl-1,1,3,3,3-pentafluoropropyl)cyclohexan-1-ol Reaction was performed as in <1-2> of Example 1 aside from using 272 g of the ketoalcohol compound equivalent obtained in <2-1> instead of the ketoalcohol compound equivalent obtained in <1-1>. A crude product was obtained. Recrystallization from n-hexane gave 217 g (yield 80%) of the target diol compound.

1-(2-hydroxy-2-methyl-1,1,3,3,3-pentafluoropropyl)-cyclohexan-1-ol colorless solid IR (KBr): ν=3448, 3195, 2968, 2954, 2945, 2873, 2861, 1303, 1176, 1087, 1054, 985 cm$^{-1}$ $^1$H-NMR (600 MHz in DMSO-d6): δ=1.08-1.18 (1H, m), 1.45-1.63 (10H, m), 1.81 (1H, d-like, J=12 Hz), 2.02 (1H, d-like, J=13 Hz), 5.16 (1H, br. s, OH), 6.69 (1H, s, OH) ppm $^{13}$C-NMR (150 MHz in DMSO-d6): δ=20.15, 21.83, 21.95, 26.51, 31.33, 32.25, 76.42 (t, J=25 Hz), 77.67 (hex-like, J=26 Hz), 122.31 (dd, J=258, 263 Hz), 126.52 (q, J=290 Hz) ppm $^{19}$F-NMR (565 MHz in DMSO-d6, trifluoroacetic acid standard): δ=−120.5 (1F, dq, J=262, 13 Hz), −118.3 (1F, dq, J=262, 15 Hz), −77.3 (3F, t-like, J=14 Hz) ppm <2-3> Synthesis of 1-(2-hydroxy-2-methyl-1,1,3,3,3-pentafluoropropyl)-1-cyclohexyl methacrylate Reaction was performed as in <1-3> of Example 1 aside from using 144 g of the diol compound obtained in <2-2> instead of the diol compound obtained in <1-2>. A crude product was obtained. In this example, the stirring time at room temperature was 18 hours, and the target compound was obtained with little of the regioisomer. Recrystallization from n-hexane gave 154 g (yield 85%) of the target fluorinated ester compound.

1-(2-hydroxy-2-methyl-1,1,3,3,3-pentafluoropropyl)-1-cyclohexyl methacrylate colorless solid GC-MS (EI): (m/z)$^+$=41, 69, 87, 111, 131, 224, 330 (M$^+$)

IR (KBr): ν=3390, 3025, 3000, 2942, 2873, 1706, 1463, 1328, 1164, 1128, 1062 cm$^{-1}$ $^1$H-NMR (600 MHz in DMSO-d6): δ=1.23-1.30 (2H, m), 1.32-1.41 (1H, m), 1.51 (3H, s), 1.57-1.70 (5H, m), 1.92 (3H, s), 2.70-2.75 (1H, m), 2.78-2.83 (1H, m), 5.74 (1H, quint-like, J=1 Hz), 6.08 (1H, q-like, J=0.7 Hz), 7.09 (1H, s) ppm $^{13}$C-NMR (150 MHz in DMSO-d6): δ=19.46, 19.67, 22.30, 22.38, 25.67, 29.79, 31.41, 77.80 (hex, J=27 Hz), 86.79 (t, J=27 Hz), 121.23 (t, J=262 Hz), 126.15 (q, J=289 Hz), 127.36, 138.16, 165.71 ppm $^{19}$F-NMR (565 MHz in DMSO-d6, trifluoroacetic acid standard): δ=−112.8 to −112.9 (2F, m), −77.1 (t, J=14 Hz) ppm Example 3

Synthesis of 1-(1,1,3,3,3-pentafluoro-2-trimethylsilyloxy-propyl)-1-cyclohexyl methacrylate

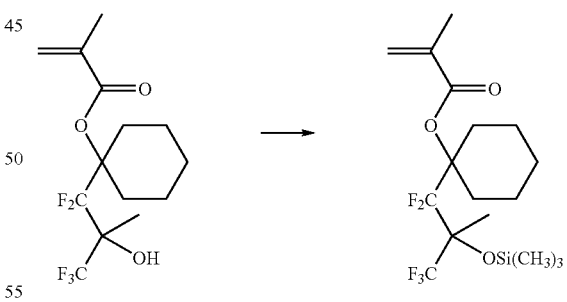

With stirring at room temperature under nitrogen atmosphere, 38.3 ml of trimethylsilyl chloride was added dropwise to a solution of 50.0 g of the fluorinated ester compound obtained in <2-3> of Example 2 and 41.2 g of imidazole in 300 g of N,N-dimethylformamide. Stirring continued at room temperature for 16 hours. The reaction mixture was mixed with 500 ml of water and extracted with diethyl ether. Through conventional work-up procedure including washing, drying and concentration, there was obtained 59.0 g (yield 97%) of the target fluorinated ester compound having a hydroxyl group protected.

1-(1,1,3,3,3-pentafluoro-2-trimethylsilyloxypropyl)-1-cyclohexyl methacrylate colorless liquid IR (NaCl): ν=2944, 2865, 1735, 1454, 1257, 1195, 1184, 1159, 1147, 1132, 1058, 981 cm$^{-1}$ $^1$H-NMR (600 MHz in DMSO-d6): δ=0.17 (9H, s), 1.18-1.36 (3H, m), 1.50-1.64 (8H, m), 3.23 (3H, s), 2.61 (1H, d-like, J=12 Hz), 2.79 (1H, d-like, J=13 Hz), 5.69 (1H, t, J=1.4 Hz), 6.03 (1H, s) ppm $^{13}$C-NMR (150 MHz in DMSO-d6): δ=1.58, 18.10 (2C), 20.82, 20.91, 24.08, 28.72, 29.44, 79.50 (hex, J=29 Hz), 84.91 (t, J=27 Hz), 119.09 (t, J=263 Hz), 123.95 (q, J=286 Hz), 125.93, 136.59, 164.13 ppm $^{19}$F-NMR (565 MHz in DMSO-d6, trifluoroacetic acid standard): δ=−111.93 (1F, dq, J=273, 11 Hz), −111.35 (1F, dq, J=273, 11 Hz), −76.30 (3F, t, J=11 Hz) ppm Example 4

Synthesis of 1-(2-methoxymethoxy-1,1,3,3,3-pentafluoro-propyl)-1-cyclohexyl methacrylate

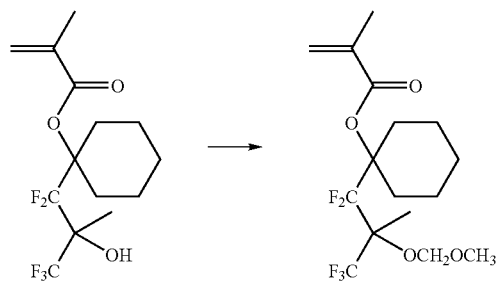

With stirring at room temperature under nitrogen atmosphere, 4.6 ml of chloromethyl methyl ether was added dropwise to a solution of 5.0 g of the fluorinated ester compound obtained in <2-3> of Example 2, 0.1 g of sodium iodide, and 12.6 ml of diisopropylethylamine in 30 g of acetonitrile. The mixture was slowly heated to 70° C., at which stirring continued for 16 hours. The reaction mixture was cooled, mixed with 500 ml of water and extracted with diethyl ether. Through conventional work-up procedure including washing, drying and concentration and purification by silica gel column chromatography, there was obtained 4.6 g (yield 81%) of the target fluorinated ester compound having a hydroxyl group protected.

1-(2-methoxymethoxy-1,1,3,3,3-pentafluoropropyl)-1-cyclohexyl methacrylate colorless liquid GC-MS (EI): (m/z)$^+$=45, 69, 101, 131, 167, 256, 284, 313, 344

GC-MS (CI, isobutane): (m/z)$^+$=101, 131, 267, 375 [(M+1)$^+$]

IR (NaCl): ν=2996, 2940, 2865, 1733, 1454, 1321, 1299, 1911, 1160, 1143, 1070 cm$^{-1}$ $^1$H-NMR (600 MHz in DMSO-d6): δ=1.23-1.37 (3H, m), 1.56-1.70 (8H, m), 1.92 (3H, t, J=1.2 Hz), 2.75 (2H, br. d, J=13 Hz), 3.35 (3H, s), 4.80 (1H, d, J=7 Hz), 4.97 (1H, d, J=7 Hz), 5.75 (1H, t, J=1.7 Hz), 6.09 (1H, q, J=1.0 Hz) ppm $^{13}$C-NMR (150 MHz in DMSO-d6): δ=14.34, 19.59, 22.25, 22.40, 25.59, 30.46, 57.25, 82.68 (q-like, J=27 Hz), 86.45 (t, J=27 Hz), 93.84, 116.58 (d, J=167 Hz), 120.87 (t, J=263 Hz), 125.40 (q, J=288 Hz), 127.51, 138.05, 165.72 ppm $^{19}$F-NMR (565 MHz in DMSO-d6, trifluoroacetic acid standard): δ=−110.40 (2F, q, J=11 Hz), −75.36 (3F, t, J=11 Hz) ppm Example 5

Synthesis of 1-(2-hydroxy-1,1,3,3,3-pentafluoropropyl)-1-cyclohexyl methacrylate

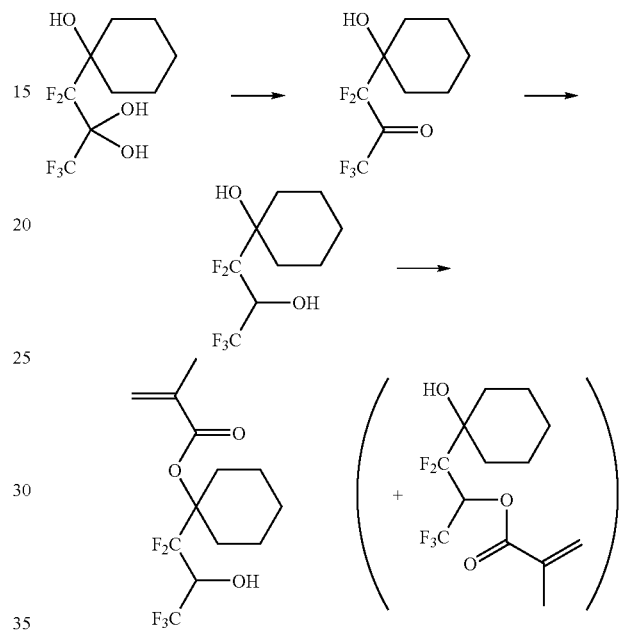

<5-1> Synthesis of 1-(2-hydroxy-1,1,3,3,3-pentafluoro-propyl)cyclohexan-1-ol

In 200 ml of benzene was dissolved 24.1 g of the hydrate of ketoalcohol compound equivalent obtained in <2-1> of Example 2. The solution was stirred and heated under reflux while the water formed was continuously removed. With stirring at 5° C. under nitrogen atmosphere, the solution was added dropwise to a suspension of 9.0 g of lithium aluminum hydride in 200 ml of tetrahydrofuran. The mixture was stirred at room temperature for 30 minutes, and then heated under reflux for 4 hours. The reaction mixture was cooled, mixed with 50 ml of acetone, then with 250 ml of 20% hydrochloric acid, and extracted with diethyl ether. Through conventional work-up procedure including washing, drying and concentration, a crude product was obtained. Recrystallization from n-hexane gave 15.0 g (yield 66%) of the target diol compound.

1-(2-hydroxy-1,1,3,3,3-pentafluoropropyl)cyclohexan-1-ol colorless solid

GC-MS (EI): (m/z)$^+$=43, 55, 81, 99

IR (KBr): ν=3490, 3394, 3172, 2950, 2873, 1378, 1286, 1182, 1122, 1093 cm$^{-1}$ $^1$H-NMR (600 MHz in DMSO-d6): δ=1.10-1.19 (1H, m), 1.37 (1H, dt-like, J=3.5, 13 Hz), 1.45-1.64 (6H, m), 1.73 (1H, d-like, J=13 Hz), 1.82 (1H, dd-like, J=2.0, 13 Hz), 4.63-4.72 (1H, m), 5.30 (1H, s, OH), 7.01 (1H, d, J=8.2 Hz, OH) ppm $^{13}$C-NMR (150 MHz in DMSO-d6): δ=21.74, 21.89, 26.45, 29.85 (d, J=5.8 Hz), 31.69 (d, J=2.9 Hz), 67.0-68.2 (m), 74.16 (t, J=24 Hz), 121.93 (dd, J=251, 264 Hz), 125.67 (q, J=285 Hz) ppm $^{19}$F-NMR (565 MHz in DMSO-d6, trifluoroacetic acid standard): δ=−127.87 (1F, dd, J=17, 258 Hz), −123.52 (1F, dq, J=17, 255 Hz), −73.52 (3F, dt, J=17, 7 Hz) ppm <5-2> Synthesis of 1-(2-hydroxy-1,1,3,3,3-pentafluoropropyl)-1-cyclohexyl methacrylate

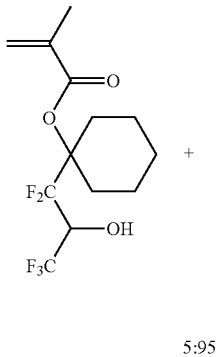

5:95

Reaction was performed as in <1-3> of Example 1 aside from using 10 g of the diol compound obtained in <5-1> instead of the diol compound obtained in <1-2>. A crude product was obtained. In this example, the stirring time at room temperature was 120 hours, and the crude product was a 5:95 mixture of the target compound and the regioisomer. By silica gel chromatography, the crude product was separated into 550 mg (yield 4%) of the target compound (fluorinated ester compound) and 8.0 g (yield 63%) of the regioisomer.

1-(2-hydroxy-1,1,3,3,3-pentafluoropropyl)-1-cyclohexyl methacrylate (target compound)
colorless viscous liquid
GC-MS (EI): (m/z)$^+$=41, 69, 87, 131, 210
$^1$H-NMR (600 MHz in DMSO-d6): δ=1.32-1.43 (2H; m), 1.45-1.71 (6H, m), 1.93 (3H, s), 2.54-2.65 (2H, m), 4.66 (1H, dq, J=29, 8 Hz), 5.73 (1H, t, J=1.5 Hz), 6.10 (1H, q, J=1, 1.7 Hz), 7.32 (1H, d, J=8 Hz, OH) ppm
$^{13}$C-NMR (150 MHz in DMSO-d6): δ=19.63, 22.33, 22.68, 25.66, 29.57, 30.36, 68.40-69.40 (m), 85.68 (t, J=25 Hz), 120.44 (dd, J=254, 263 Hz), 125.24 (q, J=285 Hz), 127.45, 138.04, 166.26 ppm
$^{19}$F-NMR (565 MHz in DMSO-d6, trifluoroacetic-acid standard): δ=−122.40 (1F, ddq-like, J=264, 22, 9 Hz), −115.72 (1F, dq-like, J=264, 17 Hz), −73.57 (3F, dt-like, J=17, 9 Hz) ppm 3-(1-hydroxycyclohexyl)-1,1,1,3,3-pentafluoro-2-propyl methacrylate (regioisomer)
colorless viscous liquid
GC-MS (EI): (m/z)$^+$=41, 69, 81, 99, 316 (M$^+$)
IR (NaCl): ν=3531, 2940, 2865, 1745, 1637, 1454, 1382, 1336, 1280, 1189, 1139, 1052 cm$^{-1}$
$^1$H-NMR (600 MHz in DMSO-d6): δ=1.08-1.17 (1H, m), 1.35-1.41 (2H, m), 1.41-1.64 (6H, m), 1.73-1.78 (1H, m), 1.97 (3H, dd, J=1.0, 1.4 Hz), 5.63 (1H, s), 5.97 (1H, quint-like, J=1.4 Hz), 6.05-6.12 (1H, m), 6.23 (1H, t-like, J=1.0 Hz) ppm
$^{13}$C-NMR (150 MHz in DMSO-d6): δ=19.10, 21.55, 21.67, 26.14, 29.83 (d, J=4.3 Hz), 30.68, 65.9-67.0 (m), 74.07 (t, J=24 Hz), 121.04 (dd, J=251, 265 Hz), 123.77 (q, J=283 Hz), 130.90, 135.32, 165.35 ppm
$^{19}$F-NMR (565 MHz in DMSO-d6, trifluoroacetic acid standard): δ=−123.86 (1F, dd-like, J=13, 264 Hz), −121.25 (1F, dq-like, J=264, 17 Hz), −72.11 (3F, dt-like, J=17, 6.5 Hz) ppm Example 6

Synthesis of 1-(2-hydroxy-1,1,3,3,3-pentafluoropropyl)-1-cyclohexyl methacrylate (exemplary use of protective group)

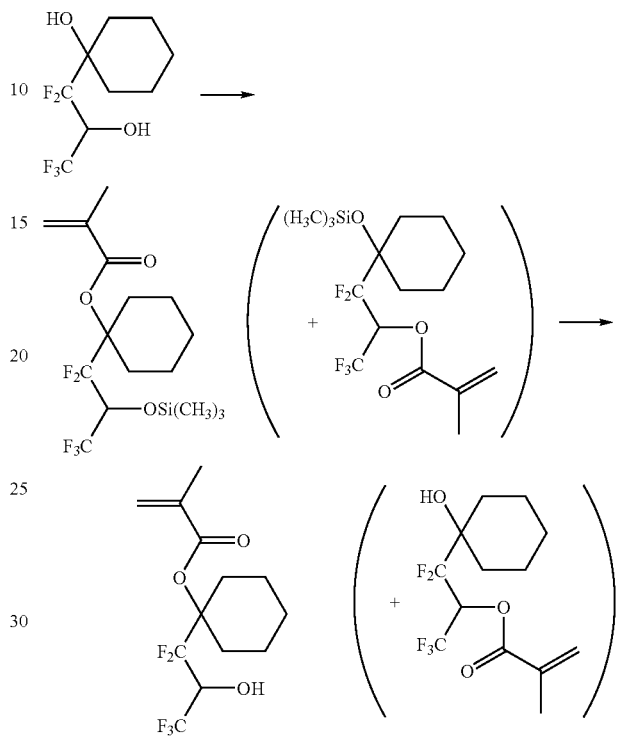

<6-1> Synthesis of 1-(1,1,3,3,3-pentafluoro-2-trimethyl-silyloxypropyl)-1-cyclohexyl methacrylate With stirring at 5° C. under nitrogen atmosphere, 1.03 ml of chlorotrimethylsilane was added dropwise to a mixture of 2.0 g of the diol compound obtained in <5-1> of Example 5, 20 ml of triethylamine, 20 ml of methylene chloride and 5 ml of tetrahydrofuran. The mixture was warmed to room temperature before it was stirred for one hour. Thereafter, 650 μl of methacryloyl chloride was added to the reaction mixture, which was heated at 70° C. and stirred for 30 hours. After cooling, the reaction mixture was mixed with 80 ml of water and extracted with methylene chloride. Through conventional work-up procedure including washing, drying and concentration, a crude product was obtained. It was used in the subsequent step without purification.

1-(1,1,3,3,3-pentafluoro-2-trimethylsilyloxypropyl)-1-cyclohexyl methacrylate
GC-MS (EI): (m/z)$^+$=41, 69, 87, 131, 193, 213, 282, 388 (M$^+$)

<6-2> Synthesis of 1-(2-hydroxy-1,1,3,3,3-pentafluoropropyl)-1-cyclohexyl methacrylate A tetrahydrofuran solution of 1.0M tetra-n-butylammonium fluoride, 10 ml, was added to a solution of the crude product of <6-1> in 6 ml of tetrahydrofuran, followed by stirring at room temperature for 18 hours. The reaction mixture was mixed with 80 ml of 15% hydrochloric acid and extracted with ethyl acetate. Through conventional work-up procedure including washing, drying and concentration, a crude product was obtained.

The crude product was a 85:15 mixture of the target compound and its regioisomer. By silica gel chromatography, the crude product was separated into 1.7 g (yield 67%)

of the target compound (fluorinated ester compound) and 0.2 g (yield 8%) of the regioisomer. Their spectroscopic properties were identical with those of Example 5.

Example 7

Synthesis of 3-hydroxy-2,2,4,4,4-pentafluoro-1-phenylbutyl methacrylate

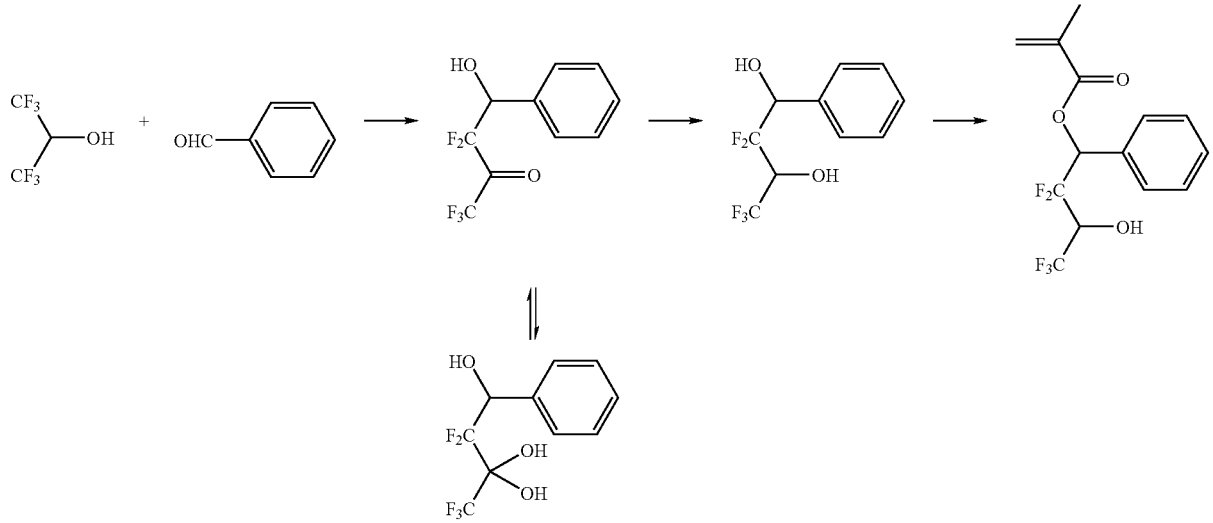

<7-1> Synthesis of 3-oxo-2,2,4,4,4-pentafluoro-1-phenyl-1-butanol equivalent

Reaction was performed as in <1-1> of Example 1 aside from using 30 g of benzaldehyde instead of the 2-adamantanone in <1-1>. A crude product was obtained. Recrystallization from n-hexane gave 62.3 g (yield 79%) of a hydrate which was an equivalent of the target ketoalcohol compound.

3,3-dihydroxy-2,2,4,4,4-pentafluoro-1-phenyl-1-butanol
colorless solid
IR (KBr): ν=3532, 1492, 1456, 1288, 1251, 1207, 1164, 1099, 1074, 1066 cm$^{-1}$
$^1$H-NMR (600 MHz in DMSO-d6): δ=5.26 (d, J=22 Hz), 6.98 (1H, br. d, J=3 Hz, OH), 7.33-7.45 (6H, m), 8.18 (1H, d, J=2 Hz) ppm
$^{19}$F-NMR (283 MHz in DMSO-d6, trifluoroacetic acid standard): δ=−128.95 (1F, ddq, J=260, 22, 10 Hz), −177.03 (1F, ddq, J=260, 10, 3 Hz), −80.31 (3F, t, J=10 Hz) ppm <7-2> Synthesis of 3-hydroxy-2,2,4,4,4-pentafluoro-1-phenyl-1-butanol Reaction was performed as in <5-1> of Example 5 aside from using 30 g of the hydrate of ketoalcohol compound equivalent obtained in <7-1> instead of the hydrate of ketoalcohol compound equivalent obtained in <2-1>. There was obtained a crude product, which was distilled in vacuo, collecting 25 g (yield 89%) of the target diol compound.

3-hydroxy-2,2,4,4,4-pentafluoro-1-phenyl-1-butanol (43:57 diastereomer mixture)
pale yellow viscous liquid
boiling point: 115° C./53 Pa
IR (NaCl): ν=3372, 2940, 1456, 1373, 1276, 1224, 1174, 1137, 1112, 1060, 1031 cm$^{-1}$ $^1$H-NMR (600 MHz in DMSO-d6): δ=4.22-4.32 (0.43H, m), 4.69 (0.57H, dq, J=30, 7 Hz), 4.99 (0.43H, dt, J=5, 13 Hz), 5.04 (0.57H, dd, J=4, 24 Hz), 6.43 (0.43H, d, J=5 Hz, OH), 6.49 (0.57H, d, J=4 Hz, OH), 7.30-7.56 (6H, m) ppm $^{13}$C-NMR (150 MHz in DMSO-d6): δ=67.5-68.5 (m, major), 68.6-69.3 (m, minor), 71.35 (dd, J=20, 32 Hz, major), 72.94 (t, J=25 Hz, minor), 120.92 (dd, J=251, 256 Hz, minor), 121.48 (t, J=254 Hz, major), 125.12 (q, J=285 Hz, minor), 125.66 (q, J=283 Hz, major), 129.31 (major+ minor), 129.46 (major), 129.50 (minor), 129.70 (minor), 129.80 (major), 138.48 (major), 138.86 (minor) ppm $^{19}$F-NMR (565 MHz in DMSO-d6, trifluoroacetic acid standard): δ=−126.51 (0.57F, dhex-like, J=258, 14 Hz), −122.72 (0.43F, dhex-like, J=256, 9 Hz), −122.64 (0.57F, dhex-like, J=256, 9 Hz), −122.02 (0.43F, dhex-like, J=256, 11 Hz), −73.70 (0.43×3F, dt-like, J=7, 15 Hz), −73.28 (0.57×3F, dt-like, J=7, 15 Hz) ppm <7-3> Synthesis of 3-hydroxy-2,2,4,4,4-pentafluoro-1-phenylbutyl methacrylate Reaction was performed as in <1-3> of Example 1 aside from using 11.1 g of the diol compound obtained in <7-2> instead of the diol compound obtained in <1-2>. A crude product was obtained. The reaction was monitored by gas chromatography, finding a higher proportion of a regioisomer at the initial (target compound:regioisomer=23:77 immediately after dropwise addition), subsequent gradual isomerization into the target compound, and substantial conversion to the target compound after 24 hours. The crude product was purified by silica gel chromatography, to give 7.5 g (yield 53%) of the target fluorinated ester compound.

3-hydroxy-2,2,4,4,4-pentafluoro-1-phenylbutyl methacrylate (40:60 diastereomer mixture)
pale yellow viscous liquid
IR (NaCl): ν=3434, 2985, 1731, 1378, 1280, 1151 cm$^{-1}$
$^1$H-NMR (600 MHz in DMSO-d6): δ=1.96 (0.4×3H, s), 1.98 (0.6×3H, s), 4.23-4.33 (0.4H, m), 4.62-4.73 (0.6H, m), 5.85-5.88 (0.4H+0.6H, m), 6.12 (0.6H, d, J=3 Hz, OH), 6.15 (0.4H, d, J=3 Hz, OH), 6.25 (0.4H, t, J=1.0 Hz), 6.26-6.32 (0.4H+0.6×2H, m), 7.20-7.78 (0.4×5H+0.6×5H, m) ppm
$^{19}$F-NMR (565 MHz in DMSO-d6, trifluoroacetic acid standard): δ=−122.50 (0.4F, ddq-like, J=260, 26, 10 Hz), −121.60 (0.6F, dhex-like, J=262, 10 Hz), −120.20 (0.6F, dhex-like, J=262, 10 Hz), −118.65 (0.4F, dquint-like, J=26, 10 Hz), −73.82 (0.4F, q-like, J=10 Hz), −73.56 (0.6F, quint-like, J=7 Hz) ppm

Example 8

Synthesis of 1-(1,1,3,3,3-pentafluoro-2-trimethylsilyloxy-propyl)-1-cyclohexyl acrylate

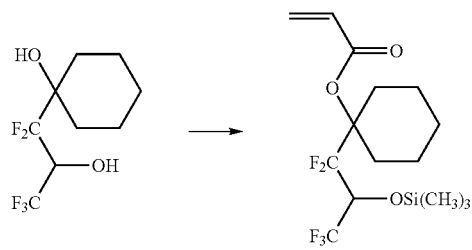

Reaction was performed as in <6-1> of Example 6 aside from using acryloyl chloride instead of the methacryloyl chloride in <6-1>. From 2.0 g of the diol compound obtained in <5-1>, 1.5 g (yield 50%) of the target fluorinated ester compound having a hydroxyl group protected was obtained.

1-(1,1,3,3,3-pentafluoro-2-trimethylsilyloxypropyl)-1-cyclohexyl acrylate

GC-MS (EI): (m/z)$^+$=55, 77, 131, 153, 193, 213, 267, 359

Example 9

Synthesis of 1-(2-hydroxy-1,1,3,3,3-pentafluoropropyl)-1-cyclohexyl acrylate

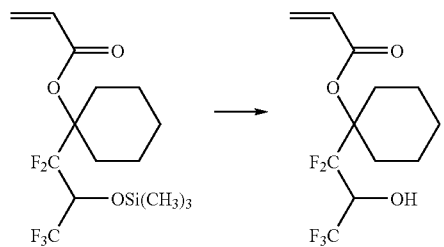

Reaction was performed as in <6-2> of Example 6 except that the fluorinated ester compound having a protected hydroxyl group obtained in Example 8 was used instead of the crude product obtained in <6-1>, obtaining the target fluorinated ester compound.

1-(2-hydroxy-1,1,3,3,3-pentafluoropropyl)-1-cyclohexyl acrylate

GC-MS (EI): (m/z)$^+$=55, 73, 131, 153, 192, 210

GC-MS (CI, isobutane): (m/z)$^+$=73, 173, 193, 211, 265, 303 [(M+H)$^+$]

Example 10

Synthesis of 1-(2-hydroxy-2-methyl-1,1,3,3,3-pentafluoro-propyl)-1-cyclohexyl α-trifluoromethylacrylate

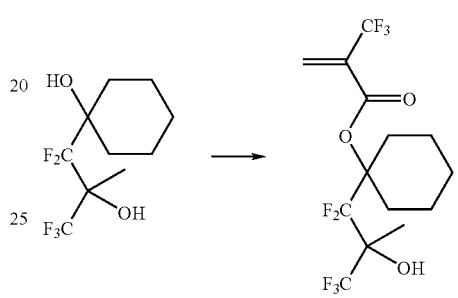

The target compound was obtained as in <1-3> of Example 1 using the diol compound obtained in <2-2> instead of the diol compound obtained in <1-2> and α-trifluoromethylacryloyl chloride instead of methacryloyl chloride.

1-(2-hydroxy-2-methyl-1,1,3,3,3-pentafluoropropyl)-1-cyclohexyl α-trifluoromethylacrylate GC-MS (EI): (m/z)$^+$=81, 123, 131, 221, 364 [(M−HF)$^+$]

GC-MS (CI, isobutane): (m/z)$^+$=141, 207, 225, 245, 385 [(M+H)$^+$]

Example 11

Synthesis of 1-ethyl-3-hydroxy-2,2,4,4,4-pentafluorobutyl methacrylate

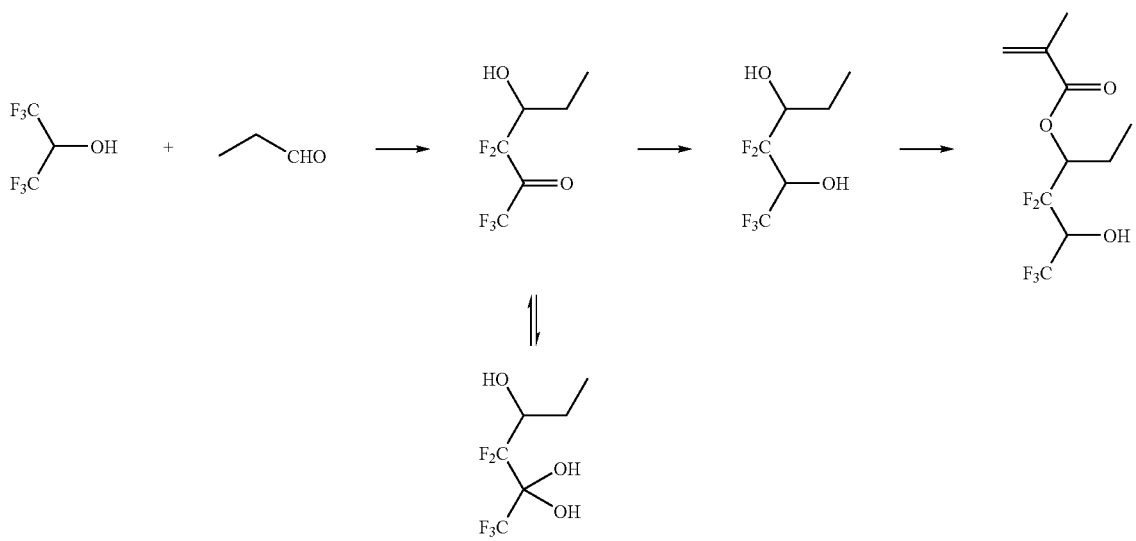

<11-1> Synthesis of 2-oxo-1,1,1,3,3-pentafluoro-4-hexanol equivalent

Synthesis was performed as in <1-1> of Example 1 aside from using propionaldehyde instead of the 2-adamantanone in <1-1>. A crude product was obtained in solid form. The crude product washed with hexane and dried in vacuo, to give a hydrate which was an equivalent of the target ketoalcohol compound, that is, 1,1,1,3,3-pentafluoro-2,2,4-hexanetriol in colorless solid form (yield 65%). The physical properties of this compound were identical with the data reported by Nakai et al., Organic Syntheses, Vol. 76, pp. 151 (1998).

the diol compound obtained in <1-2>. The resulting crude product was purified by silica gel column chromatography, to give the target fluorinated ester compound (yield 85%).

1-ethyl-3-hydroxy-2,2,4,4,4-pentafluorobutyl methacrylate (Mixture of Two Diastereomers)

colorless liquid

GC-MS (EI): (m/z)$^+$=41, 69, 87, 170, 276 (M$^+$)

GC-MS (CI, methane)=(m/z)$^+$=87, 115, 171, 237, 257, 277 [(M+H)$^+$]

Example 12

Synthesis of 1-cyclohexyl-3-hydroxy-2,2,4,4,4-pentafluorobutyl methacrylate

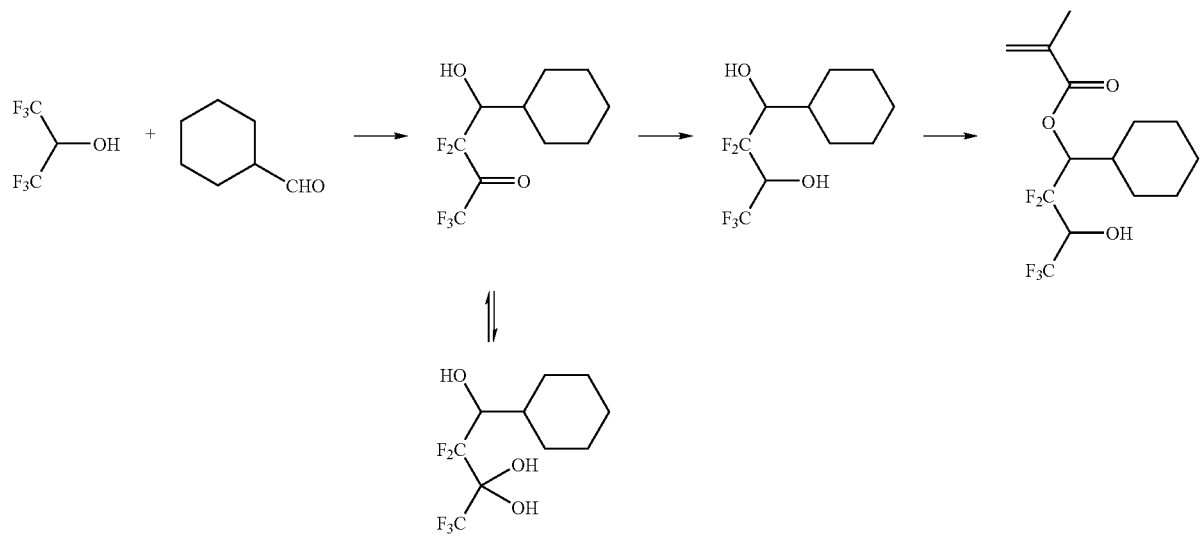

<11-2> Synthesis of 1,1,1,3,3-pentafluoro-2,4-hexanediol

A mixture of 100 g of the triol compound obtained in <11-1>, 400 g of tetrahydrofuran and 200 g of water was stirred at 5° C., to which a mixture of 17 g of sodium borohydride and 200 g of water was added dropwise over one hour. The reaction mixture was slowly warmed up to room temperature and then stirred for 16 hours. The reaction was quenched by adding 100 g of 20% hydrochloric acid. Through conventional work-up procedure including washing, drying and concentration, a crude product was obtained. Vacuum distillation gave 86 g (yield 93%) of 1,1,1,3,3-pentafluoro-2,4-hexanediol.

1,1,1,3,3-pentafluoro-2,4-hexanediol (mixture of two diastereomers)

boiling point: 82° C./600 Pa colorless solid at room temperature

IR (KBr): ν=3403 (br.), 2985, 2954, 2890, 1465, 1446, 1382, 1371, 1280, 1232, 1176, 1153, 1110, 1058, 1024, 989, 848, 840, 829, 690, 680 cm$^{-1}$ $^1$H-NMR of major diastereomer (600 MHz in DMSO-d6): δ=0.93 (3H, t, J=7.6 Hz), 1.42 (1H, m), 1.60 (1H, m), 3.72 (1H, m), 4.50 (1H, m), 5.57 (1H, d, J=6.5 Hz), 7.13 (1H, d, J=7.9 Hz) ppm <11-3> Synthesis of 1-ethyl-3-hydroxy-2,2,4,4,4-pentafluorobutyl methacrylate Synthesis was performed as in <1-3> of Example 1 aside from using the diol compound obtained in <11-2> instead of <12-1> Synthesis of 1-cyclohexyl-2-oxo-2,2,4,4,4-pentafluoro-1-butanol equivalent Synthesis was performed as in <1-1> of Example 1 aside from using cyclohexanecarbaldehyde instead of the 2-adamantanone in <1-1>. There was obtained a hydrate which was an equivalent of the target ketoalcohol compound (yield 72%).

1-cyclohexyl-2,2,4,4,4-pentafluorobutane-1,3,3-triol colorless solid

IR (KBr): ν=3558, 3334 (br.), 3093, 2942, 2859, 1454, 1373, 1303, 1216, 1207, 1164, 1116, 1099, 1074, 1068, 1043, 993, 887, 871, 796, 734 cm$^{-1}$ $^1$H-NMR (600 MHz in DMSO-d6): δ=1.02-1.32 (5H, m), 1.53 (1H, m), 1.58 (1H, m), 1.69 (2H, m), 1.77 (2H, m), 3.88 (1H, m), 5.83 (1H, d, J=6.5 Hz), 7.50 (1H, s), 7.90 (1H, d, J=1.0 Hz) ppm <12-2> Synthesis of 1-cyclohexyl-2,2,4,4,4-pentafluorobutane-1,3-diol Synthesis was performed as in <11-2> of Example 11 aside from using the triol compound obtained in <12-1> instead of the triol compound obtained in <11-1>. The target diol compound was obtained in a quantitative yield.

1-cyclohexyl-2,2,4,4,4-pentafluorobutane-1,3-diol (mixture of two diastereomers)

colorless solid

IR (KBr): ν=3394 (br.), 3257 (br.), 2931, 2859, 1456, 1417, 1378, 1359, 1268, 1224, 1193, 1184, 1151, 1118, 1091, 1056, 1025, 998, 948, 881, 869, 831, 705, 682 cm$^{-1}$ $^1$H-NMR of major diastereomer (600 MHz in DMSO-d6): δ=1.00-1.30 (5H, m), 1.55-1.80 (6H, m), 3.54 (1H, ddt, J=6.9, 2.4, 9.7 Hz), 4.49 (1H, m), 5.48 (1H, d, J=6.9 Hz), 7.14 (1H, d, J=7.9 Hz) ppm <12-3> Synthesis of 1-cyclohexyl-3-hydroxy-2,2,4,4,4-pentafluorobutyl methacrylate Synthesis was performed as in <1-3> of Example 1 aside from using the diol compound obtained in <12-2> instead of the diol compound obtained in <1-2>. The resulting crude product was purified by silica gel column chromatography, to give the target fluorinated ester compound (yield 75%).

1-cyclohexyl-3-hydroxy-2,2,4,4,4-pentafluorobutyl methacrylate (mixture of two diastereomers)

colorless liquid

IR (NaCl): ν=3446 (br.), 2933, 2858, 1710, 1637, 1454, 1380, 1351, 1278, 1226, 1170, 1112, 1027, 950, 827, 686 cm$^{-1}$ $^1$H-NMR of major diastereomer (600 MHz in DMSO-d6): δ=0.95-1.30 (5H, m), 1.58 (2H, m), 1.67 (2H, m), 1.79 (1H, m), 1.90-2.00 (4H, m), 4.70 (1H, m), 5.27 (1H, ddd, J=19.9, 8.3, 2.8 Hz), 5.77 (1H, m), 6.11 (1H, m), 7.55 (1H, d, J=7.6 Hz) ppm $^{13}$C-NMR (150 MHz in DMSO-d6): δ=17.84, 17.93, 25.30, 25.45, 25.55, 25.67, 25.91, 25.93, 27.10, 30.14, 36.49, 36.51, 36.63, 67.23 (m), 67.89 (m), 72.58 (dd, J=32, 22 Hz), 73.57 (t, J=21 Hz), 119.84 (t, J=255 Hz), 120.38 (t, J=254 Hz), 123.53 (q, J=284 Hz), 123.70 (q, J=284 Hz), 126.81, 135.18, 135.21, 165.10, 165.59 ppm $^{19}$F-NMR (565 MHz in DMSO-d6, trifluoroacetic acid standard): δ=−120.97 (0.35F, dm, J=262 Hz), −117.97 (0.35F, dm, J=262 Hz), −117.35 (0.65F, dm, J=259 Hz), −115.28 (0.65F, dm, J=259 Hz), −73.70 (1.95F, m), 73.54 (1.05F, m) ppm Example 13

Synthesis of 1-(2-adamantyl)-3-hydroxy-2,2,4,4,4-pentafluorobutyl methacrylate

<13-1> Synthesis of 1-(2-adamantyl)-3-oxo-2,2,4,4,4-pentafluoro-1-butanol equivalent Synthesis was performed as in <1-1> of Example 1 aside from using 2-adamantanecarbaldehyde instead of the 2-adamantanone in <1-1>. There was obtained an equivalent of the target ketoalcohol compound in hydrate form (yield 73%).

1-(2-adamantyl)-2,2,4,4,4-pentafluorobutane-1,3,3-triol colorless solid

IR (KBr): ν=3563, 3450 (br.), 3384 (br.), 2917, 2854, 1456, 1380, 1276, 1230, 1213, 1199, 1182, 1139, 1091, 1054, 1035, 997, 973, 937, 908, 877, 829, 709 cm$^{-1}$ $^1$H-NMR (600 MHz in DMSO-d6): δ=1.50-1.58 (2H, m), 1.70-1.77 (4H, m), 1.77-1.94 (6H, m), 2.02 (1H, m), 2.06-2.12 (2H, m), 4.43 (1H, m), 6.53 (1H, br. d, J=5.5 Hz), 7.43 (1H, br. s), 8.04 (1H, br. s) ppm <13-2> Synthesis of 1-(2-adamantyl)-2,2,4,4,4-pentafluorobutane-1,3-diol Synthesis was performed as in <11-2> of Example 11 aside from using the triol compound obtained in <13-1> instead of the triol compound obtained in <11-1>. The target diol compound was obtained in a quantitative yield.

1-(2-adamantyl)-2,2,4,4,4-pentafluorobutane-1,3-diol (mixture of two diastereomers)

colorless solid

IR (KBr): ν=3426 (br.), 3249 (br.), 2908, 2850, 1456, 1378, 1274, 1230, 1203, 1174, 1141, 1120, 1106, 1091, 1074, 1056, 1041, 1034, 1002, 885, 844, 819 cm$^{-1}$ $^1$H-NMR (600 MHz in DMSO-d6): δ=1.45-1.50 (2H, m), 1.60-1.90 (10H, m), 1.90-2.05 (2H, m), 2.07 (1H, m), 3.94 (0.74H, m), 4.08 (0.26H, dt, J=24.1, 9.1 Hz), 4.50-4.60 (1H, m), 5.49 (0.26H, br. d, J=8.6 Hz), 5.72 (0.74H, d, J=7.2 Hz), 7.07 (0.74H, d, J=7.6 Hz), 7.19 (0.26H, br. d, J=7.2 Hz) ppm <13-3> Synthesis of 1-(2-adamantyl)-3-hydroxy-2,2,4,4,4-pentafluorobutyl methacrylate Synthesis was performed as in <1-3> of Example 1 aside from using the diol compound obtained in <13-2> instead of the diol compound obtained in <1-2>. The resulting crude product was purified by silica gel column chromatography, to give the target fluorinated ester compound (yield 81%).

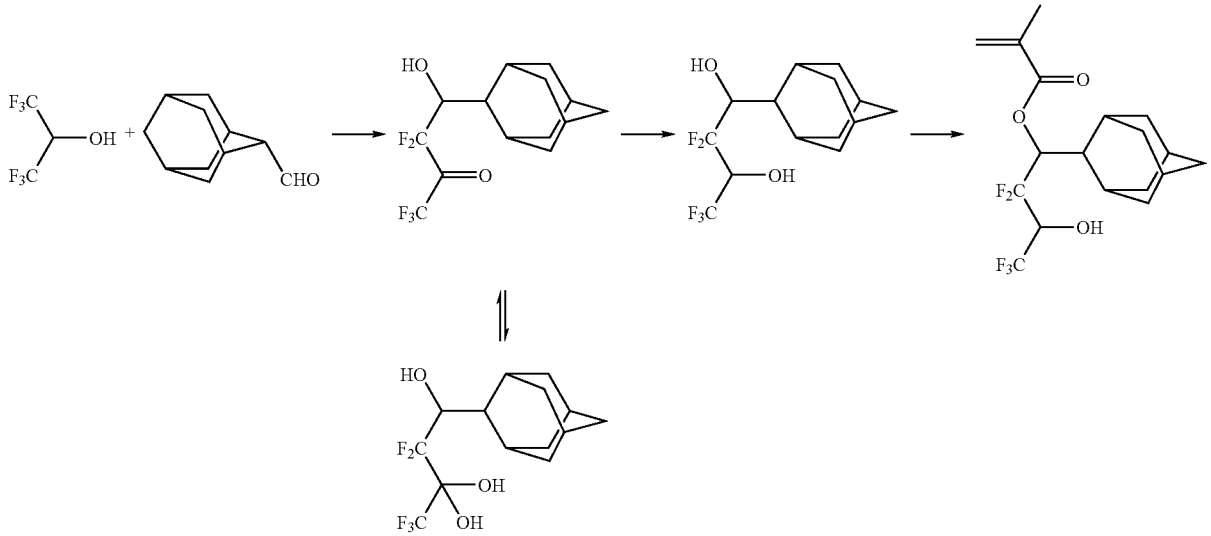

1-(2-adamantyl)-3-hydroxy-2,2,4,4,4-pentafluorobutyl methacrylate (mixture of two diastereomers)

colorless liquid

IR (NaCl): ν=3446 (br.), 2912, 2856, 1710, 1637, 1456, 1380, 1342, 1276, 1218, 1168, 1116, 1025, 946, 819, 811 cm$^{-1}$ $^1$H-NMR (600 MHz in DMSO-d6): δ=1.46 (1H, m), 1.59 (1H, m), 1.68-1.89 (10H, m), 1.90 (3H, m), 2.07 (1H, m), 2.22 (0.24H, br. d, J=10.3 Hz), 2.33 (0.76H, br. d, 10.0 Hz), 4.28 (0.24H, m), 4.51 (0.76H, m), 5.60-5.70 (1H, m), 5.73 (0.24H, br. s), 5.76 (0.76H, br. s), 6.09 (0.24H, br. s), 6.11 (0.76H, br. s), 7.28 (0.24H, d, J=7.9 Hz), 7.38 (0.76H, d, J=7.9 Hz) ppm $^{13}$C-NMR (150 MHz in DMSO-d6): δ=17.59, 17.72, 26.56, 26.66, 26.91, 27.47, 27.61, 28.27 (d-like, J=5 Hz), 28.47 (d-like, J=4 Hz), 31.24, 31.34, 31.45, 31.49, 37.08, 37.09, 37.77, 37.89, 38.03, 38.07, 89.08, 39.22, 42.97 (d-like, J=2 Hz), 42.57 (d-like, J=3 Hz), 67.10 (ddq, J=22, 30, 30 Hz), 67.72 (m), 69.68 (dd, J=32, 26 Hz), 71.43 (dd, J=27, 24 Hz), 119.46 (dd, J=258, 251 Hz), 120.73 (t, J=255 Hz), 123.32 (q, J=285 Hz), 123.51 (q, J=285 Hz), 126.50, 126.75, 134.89, 135.07, 164.68, 169.97 ppm $^{19}$F-NMR (565 MHz in DMSO-d6, trifluoroacetic acid standard):

δ=−119.08 (0.24F, dm, J=264 Hz), −118.98 (0.76F, dm, J=265 Hz), −118.42 (0.24F, dm, J=264 Hz), −112.92 (0.76F, dm, J=265 Hz), −73.5-73.4 (3F, m) ppm Example 14

Synthesis of 1-(1-adamantyl)-3-hydroxy-2,2,4,4,4-pentafluorobutyl methacrylate

<14-1> Synthesis of 1-(1-adamantyl)-3-oxo-2,2,4,4,4-pentafluoro-1-butanol equivalent Synthesis was performed as in <1-1> of Example 1 aside from using 1-adamantanecarbaldehyde instead of the 2-adamantanone in <1-1>. There was obtained an equivalent of the target ketoalcohol compound in hydrate form (yield 83%).

1-(1-adamantyl)-2,2,4,4,4-pentafluorobutane-1,3,3-triol colorless solid

IR (KBr): ν=3411 (br.), 3243 (br.), 2908, 2850, 1454, 1344, 1290, 1267, 1211, 1193, 1149, 1110, 1093, 1072, 1039, 867 cm$^{-1}$ $^1$H-NMR (600 MHz in DMSO-d6): δ=1.60 (3H, dm, J=11.3 Hz), 1.65 (3H, dm, J=11.3 Hz), 1.68 (3H, dm, J=14.1 Hz), 1.69 (3H, dm, J=14.1 Hz), 1.98 (3H, m), 3.71 (1H, br. d, J=27 Hz), 6.38 (1H, br.), 7.33 (1H, br.), 8.00 (1H, br.) ppm <14-2> Synthesis of 1-(1-adamantyl)-2,2,4,4,4-pentafluorobutane-1,3-diol Synthesis was performed as in <11-2> of Example 11 aside from using the triol compound obtained in <14-1> instead of the triol compound obtained in <11-1>. The target diol compound was obtained (yield 99%).

1-(1-adamantyl)-2,2,4,4,4-pentafluorobutane-1,3-diol (mixture of two diastereomers)

colorless solid

IR (KBr): ν=3482 (br.), 3376 (br.), 2906, 2850, 1450, 1407, 1361, 1265, 1203, 1187, 1160, 1147, 1137, 1103, 1087, 1054, 1045, 1024, 987, 971, 877, 833, 819, 761 cm$^{-1}$ $^1$H-NMR of major diastereomer (600 MHz in DMSO-d6): δ=1.61 (3H, dm, J=11.7 Hz), 1.64 (3H, dm, J=11.7 Hz), 1.67 (3H, dm, J=12.7 Hz), 1.72 (3H, dm, J=12.7 Hz), 1.92 (3H, m), 3.23 (1H, dm, J=24.4 Hz), 4.53 (1H, m), 5.58 (1H, br. d, J=6.2 Hz), 7.01(1H, m) ppm <14-3> Synthesis of 1-(1-adamantyl)-3-hydroxy-2,2,4,4,4-pentafluorobutyl methacrylate Synthesis was performed as in <1-3> of Example 1 aside from using the diol compound obtained in <14-2> instead of the diol compound obtained in <1-2>. The resulting crude product was purified by silica gel column chromatography, to give the target fluorinated ester compound (yield 85%).

1-(1-adamantyl)-3-hydroxy-2,2,4,4,4-pentafluorobutyl methacrylate (mixture of two diastereomers)

colorless solid

IR (KBr): ν=3386 (br.), 2915, 2854, 1718, 1639, 1452, 1407, 1384, 1365, 1351, 1344, 1315, 1299, 1274, 1218, 1164, 1114, 1025, 1016, 941, 854, 827, 813, 759, 682 cm$^{-1}$

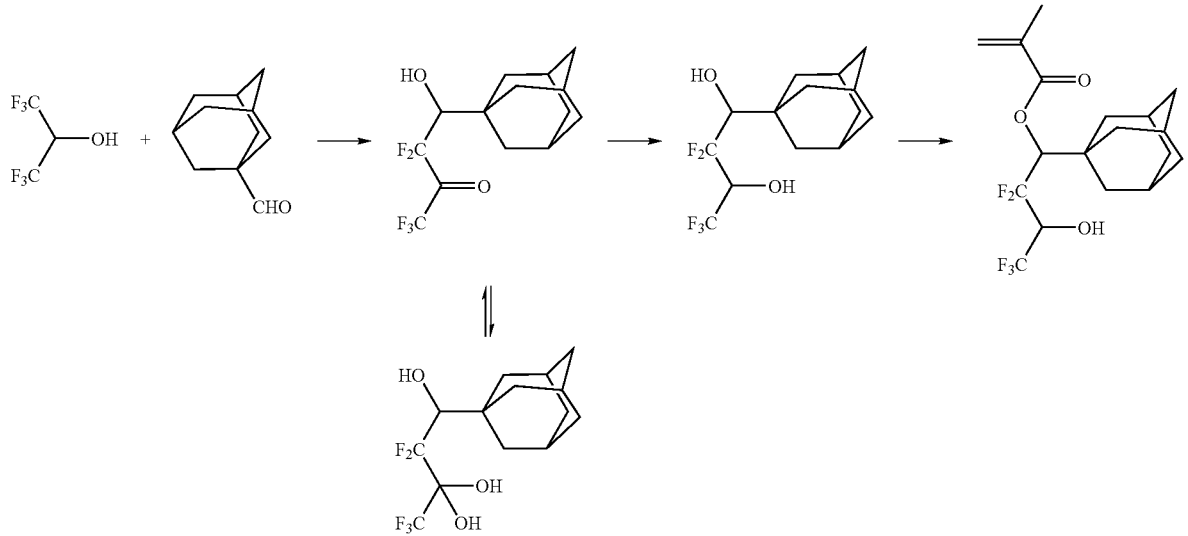

$^1$H-NMR of major diastereomer (600 MHz in DMSO-d6): δ=1.58-1.75 (12H, m), 1.90-1.95 (6H, m), 4.14 (1H, m), 5.38 (1H, dd, J=25.7, 3.1 Hz), 5.78 (1H, m), 6.13 (1H, m), 7.34 (1H, m) ppm $^{13}$C-NMR of major diastereomer (150 MHz in DMSO-d6): δ=19.51, 29.00, 37.68, 38.69, 39.53, 69.03 (ddq, J=22, 30, 30 Hz), 75.73 (dd, J=32, 22 Hz), 123.42 (t, J=257 Hz), 125.17 (q, J=285 Hz), 128.34, 136.74, 166.32 ppm $^{19}$F-NMR of major diastereomer (565 MHz in DMSO-d6, trifluoroacetic acid standard): δ=−117.77 (1F, ddq, J=262, 22, 10 Hz), −116.04 (1F, ddq, J=262, 27, 14 Hz), −73.22 (3F, ddd, J=14, 10, 8 Hz) ppm Example 15

Synthesis of 3-hydroxy-2,2,4,4,4-pentafluorobutyl methacrylate

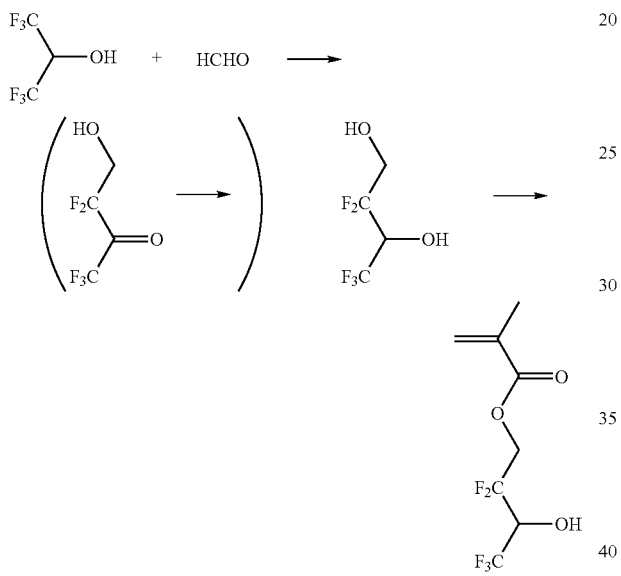

<15-1> Synthesis of 2,2,4,4,4-pentafluoro-1,3-butanediol

With stirring in a nitrogen atmosphere, a mixture of 109 g of 1,1,1,3,3,3-hexafluoro-2-propanol and 500 g of tetrahydrofuran was cooled to 5° C. To the mixture, 500 ml of 2.71M n-butyllithium in n-hexane was added dropwise. The mixture was stirred at 5° C. for 2 hours, after which 19.5 g of formaldehyde was added. The mixture was stirred at 5° C. for one hour and then at room temperature for 18 hours. To the reaction mixture, 500 g of water and a mixture of 37.0 g of sodium borohydride and 300 g of water were sequentially added dropwise. The mixture was stirred at room temperature for 10 hours. The reaction was quenched by adding 330 g of 20% hydrochloric acid. Through conventional work-up procedure including washing, drying and concentration, there was obtained a crude product. It was distilled in vacuo for purification, to give 58.3 g of the target compound, 2,2,4,4,4-pentafluoro-1,3-butanediol (boiling point 90-100° C./1660 Pa, yield 50%).

GC-MS (EI): (m/z)$^+$=30, 51, 63, 80, 113, 132

GC-MS (CI, methane): (m/z)$^+$=141, 161, 181 [(M+H)$^+$]

<15-2> Synthesis of 3-hydroxy-2,2,4,4,4-pentafluorobutyl methacrylate

A mixture of 10 g of the 2,2,4,4,4-pentafluoro-1,3-butanediol obtained in <15-1>, 9.6 g of methacrylic acid, 1.1 g of p-toluenesulfonic acid, and 30 g of toluene was heated under reflux for 3 hours while the water formed by reaction was being distilled off. The reaction mixture was cooled to room temperature and then subjected to conventional work-up procedure including washing, drying and concentration. The resulting crude product was purified by silica gel column chromatography, to give 9.9 g (yield 72%) of the target fluorinated ester compound.

3-hydroxy-2,2,4,4,4-pentafluorobutyl methacrylate colorless liquid

GC-MS (EI): (m/z)$^+$=41, 69, 86, 99, 248 (M$^+$)

GC-MS (CI, methane): (m/z)$^+$=69, 181, 209, 229, 249 [(M+H)$^+$]

Example 16

Synthesis of 2,2-dimethyl-3-hydroxy-2,2,4,4,4-pentafluoro-butyl methacrylate

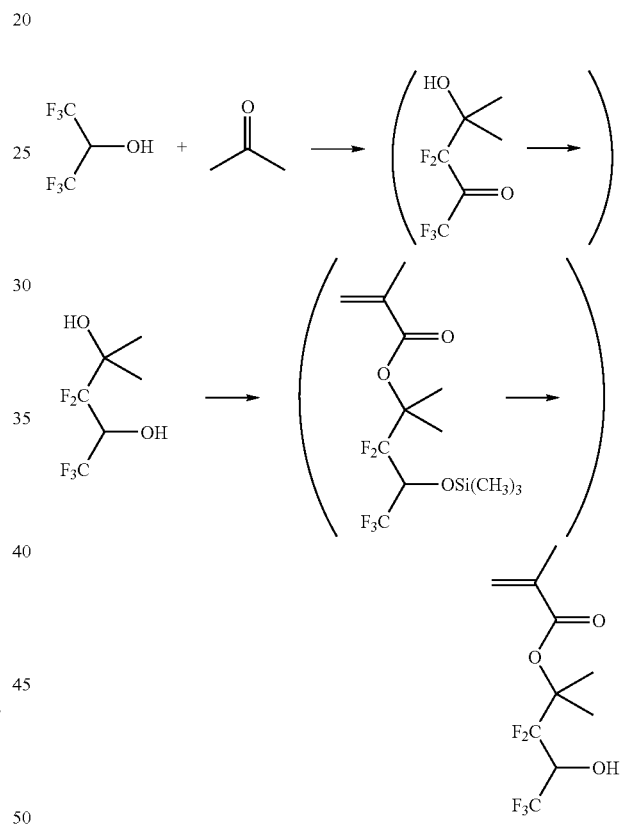

<16-1> Synthesis of 4-methyl-1,1,1,3,3-pentafluoropentane-2,4-diol

The target diol compound was obtained (yield 71%) as in <15-1> of Example 15 aside from using acetone instead of the formaldehyde.

4-methyl-1,1,1,3,3-pentafluoropentane-2,4-diol boiling point: 105° C./1730 Pa colorless solid at room temperature IR (KBr): ν=3432 (br.), 3257 (br.), 3020, 3006, 2960, 2917, 2763, 1475, 1461, 1394, 1376, 1359, 1282, 1259, 1224, 1191, 1174, 1155, 1112, 1095, 1041, 970, 877, 835, 808, 694 cm$^{-1}$ $^1$H-NMR (600 MHz in DMSO-d6): δ=1.22 (3H, s), 1.24 (3H, s), 4.62 (1H, m), 5.46 (1H, br.), 7.05 (1H, m) ppm <16-2> Synthesis of 2,2-dimethyl-3-hydroxy-2,2,4,4,4-pentafluorobutyl methacrylate With stirring at 0° C., 24 g of chlorotrimethylsilane was added dropwise to a mixture of 43 g of the 4-methyl-1,1,1,3,3-pentafluoropentane-2,4-diol obtained in <16-1>, 52 g of triethylamine and 250 g of acetonitrile. The mixture was stirred for one hour, after which 26 g of methacryloyl chloride was added dropwise. The mixture was stirred at 0° C. for 1 hour and then at room temperature for 16 hours. Then 50 g of 20% hydrochloric acid was added, followed by stirring at room temperature for 24 hours. Through conventional work-up procedure including washing, drying and concentration, there was obtained a crude product. It was distilled in vacuo, to give 36 g (yield 63%) of the target fluorinated ester compound.

2,2-dimethyl-3-hydroxy-2,2,4,4,4-pentafluorobutyl methacrylate boiling point: 56° C./40 Pa colorless liquid IR (NaCl): ν=3451 (br.), 3002, 2960, 2935, 1710, 1637, 1463, 1394, 1376, 1336, 1309, 1286, 1263, 1193, 1157, 1105, 1049, 1010, 946, 848, 825, 700, 661 cm$^{-1}$ $^1$H-NMR (600 MHz in DMSO-d6): δ=1.61 (3H, s), 1.66 (3H, s), 1.85 (3H, m), 4.71 (1H, m), 5.69 (1H, m), 5.99 (1H, m), 7.32 (1H, br. d, J=7.6 Hz) ppm $^{13}$C-NMR (150 MHz in CDCl$_3$): δ=19.29, 20.70 (dd, J=6, 4 Hz), 21.67 (m), 68.56 (ddq, J=22, 30, 30 Hz), 83.62 (dd, J=30, 24 Hz), 120.09 (dd, J=259, 255 Hz), 125.28 (q, J=285 Hz), 127.78, 137.88, 166.14 ppm $^{19}$F-NMR (565 MHz in DMSO-d6, trifluoroacetic acid standard): δ=−127.78 (1F, ddq, J=261, 21, 8 Hz), −119.57 (1F, dq, J=261, 17), −73.70 (3F, dt, J=17, 8 Hz) ppm Example 17

Synthesis of 1,3-di(trifluoromethyl)-3-hydroxy-2,2,4,4,4-pentafluorobutyl methacrylate

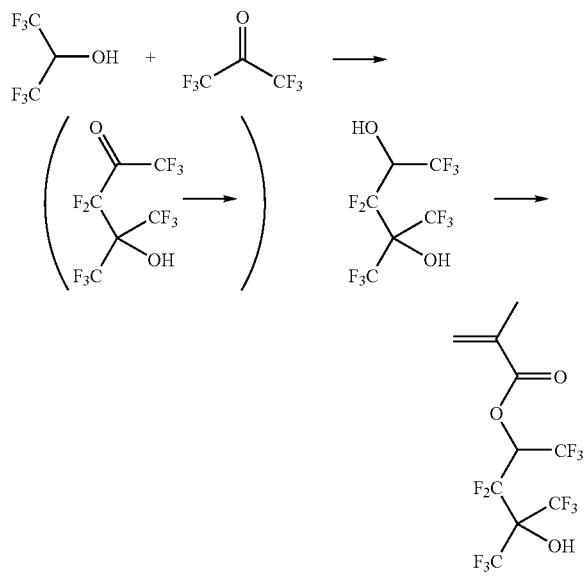

<17-1> Synthesis of 2-trifluoromethyl-1,1,1,3,3,5,5,5-octafluoropentane-2,4-diol The target diol compound was obtained (yield 67%) as in <15-1> of Example 15 aside from using hexafluoroacetone instead of the formaldehyde.

<17-2> Synthesis of 1,3-di(trifluoromethyl)-3-hydroxy-2,2,4,4,4-pentafluorobutyl methacrylate Reaction was performed as in <1-3> of Example 1 aside from using the diol compound obtained in <17-1> instead of the diol compound obtained in <1-2>. The resulting crude product was purified by silica gel column chromatography, to give the target fluorinated ester compound (yield 77%).

Example 18

Synthesis of 3-difluoromethyl-3-hydroxy-2,2,4,4,4-pentafluoro-1-trifluoromethylbutyl methacrylate

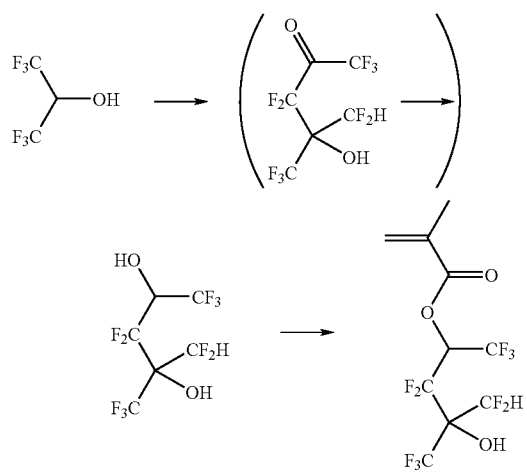

<18-1> Synthesis of 2-difluoromethyl-1,1,1,3,3,5,5,5-octafluoropentane-2,4-diol

In a nitrogen atmosphere, a mixture of 109 g of 1,1,1,3,3,3-hexafluoro-2-propanol and 500 g of tetrahydrofuran was cooled at 5° C. while stirring. To the mixture, 500 ml of 2.71M n-butyllithium in n-hexane was added dropwise, followed by stirring at 5° C. for 2 hours. To the reaction mixture, a mixture of 6.0 g of water and 50 g of tetrahydrofuran was added dropwise over 2 hours. The mixture was stirred at 5° C. for 1 hour and then at room temperature for 16 hours. To the reaction mixture, 500 g of water and a mixture of 25 g of sodium borohydride and 300 g of water were sequentially added dropwise. The mixture was stirred at room temperature for 24 hours. The reaction was quenched by adding 260 g of 20% hydrochloric acid. Through conventional work-up procedure including washing, drying and concentration, there was obtained a crude product. It was distilled in vacuo for purification, to give 53 g (yield 55%) of the target diol compound in colorless liquid form.

2-difluoromethyl-1,1,1,3,3,5,5,5-octafluoropentane-2,4-diol (mixture of two diastereomers)

boiling point: 115° C./13300 Pa colorless liquid $^1$H-NMR (600 MHz in DMSO-d6): δ=4.69 (0.7H, dm, J=14.0, HO—C$\underline{H}$), 4.78 (0.3H, dm, J=20.6 Hz, HO—C$\underline{H}$), 6.53 (0.7H, t, J=51.7 Hz, —CF$_2\underline{H}$), 6.61 (0.3H, t, J=50.8 Hz, —CF$_2\underline{H}$), 7.64 (0.7H, br., CH—O$\underline{H}$), 7.95 (0.3H, br., CH—O$\underline{H}$), 8.65 (0.7H, br. ≡C—O$\underline{H}$), 8.88 (0.3H, br. ≡C—O$\underline{H}$) ppm <18-2> Synthesis of 3-difluoromethyl-3-hydroxy-2,2,4,4,4-pentafluoro-1-trifluoromethylbutyl methacrylate Reaction was performed as in <1-3> of Example 1 aside from using the diol compound obtained in <18-1> instead of the diol compound obtained in <1-2>. The resulting crude product was purified by silica gel column chromatography, to give the target fluorinated ester compound (yield 78%).

3-difluoromethyl-3-hydroxy-2,2,4,4,4-pentafluoro-1-trifluoromethylbutyl methacrylate (mixture of two diastereomers)

colorless liquid

GC-MS (EI): (m/z)$^+$=41, 69, 86, 113, 197, 347, 366 (M$^+$)

GC-MS (CI, methane): (m/z)$^+$=69, 243, 259, 299, 347, 367 [(M+H)$^+$]

Japanese Patent Application No. 2003-348104 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymerizable fluorinated ester compound having the general formula (1) or (2):

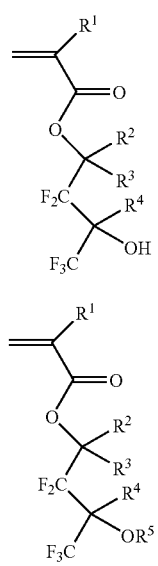

wherein R$^1$ is hydrogen, methyl or trifluoromethyl, R$^2$ and R$^3$ are each independently hydrogen or a monovalent hydrocarbon group of 1 to 15 carbon atoms which may contain at least one hetero atom, a pair of R$^2$ and R$^3$ may bond together to form a ring with the carbon atom to which they are bonded, and each of R$^2$ and R$^3$ is a divalent hydrocarbon group of 1 to 15 carbon atoms which may contain at least one hetero atom when they form a ring, R$^4$ is hydrogen, hydroxyl, or a monovalent hydrocarbon group of 1 to 15 carbon atoms which may contain at least one hetero atom, and R$^5$ is an acid labile group.

2. A process for preparing a polymerizable fluorinated ester compound having the general formula (1), comprising the steps of reacting a ketoalcohol compound having the general formula (3) with a compound of the general formula: R$^4$—Z to form a diol compound having the general formula (4), and acylating the diol compound to form a polymerizable fluorinated ester compound having the general formula (1):

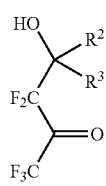

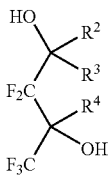

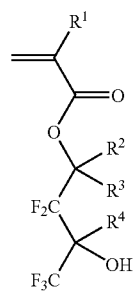

wherein R$^1$ is hydrogen, methyl or trifluoromethyl, R$^2$ and R$^3$ are each independently hydrogen or a monovalent hydrocarbon group of 1 to 15 carbon atoms which may contain at least one hetero atom, a pair of R$^2$ and R$^3$ may bond together to form a ring with the carbon atom to which they are bonded, and each of R$^2$ and R$^3$ is a divalent hydrocarbon group of 1 to 15 carbon atoms which may contain at least one hetero atom when they form a ring, R$^4$ is hydrogen, hydroxyl, or a monovalent hydrocarbon group of 1 to 15 carbon atoms which may contain at least one hetero atom, and Z is such a monovalent group that R$^4$—Z provides a R$^4$ anion equivalent.

3. A process for preparing a polymerizable fluorinated ester compound having the general formula (1), comprising the steps of reacting a ketoalcohol compound having the general formula (3) with a compound of the general formula: R$^4$—Z to form a diol compound having the general formula (4), protecting the diol compound to form an alcohol compound having the general formula (5), acylating the alcohol compound to form a protected polymerizable fluorinated ester compound having the general formula (6), and deprotecting the compound of formula (6) into a polymerizable fluorinated ester compound having the general formula (1):

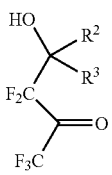

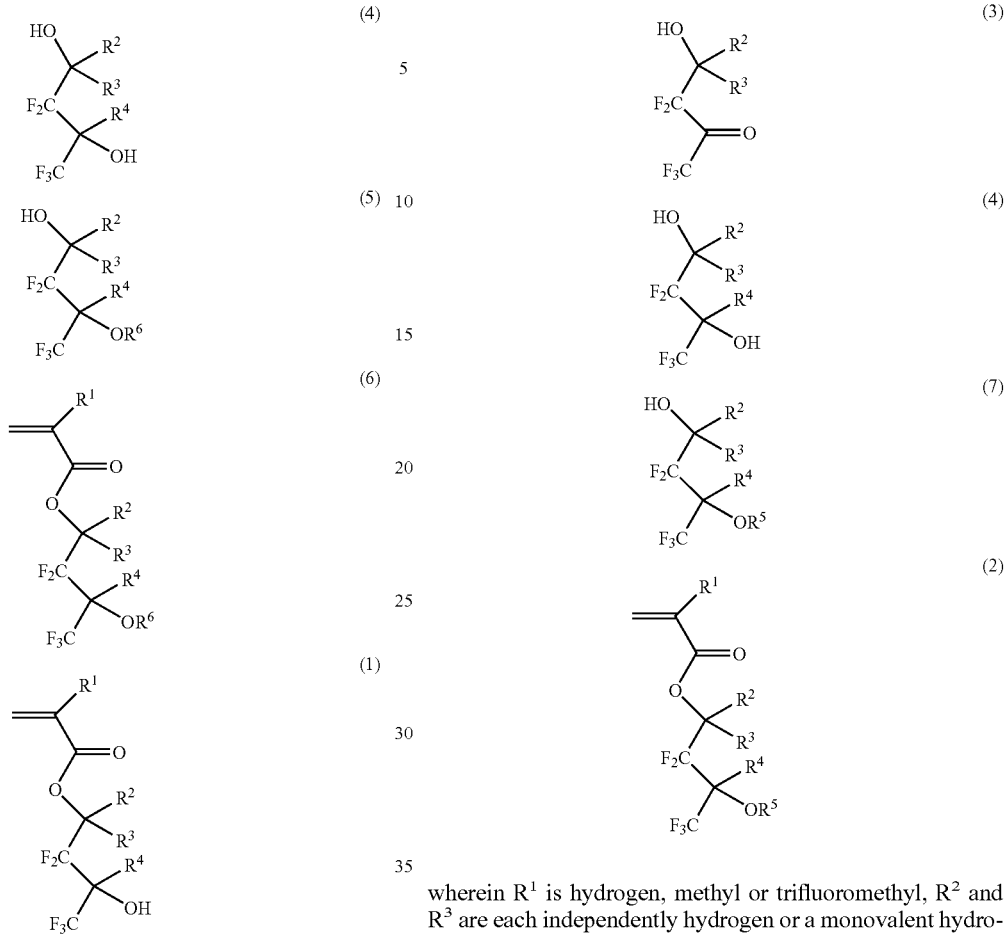

wherein $R^1$ is hydrogen, methyl or trifluoromethyl, $R^2$ and $R^3$ are each independently hydrogen or a monovalent hydrocarbon group of 1 to 15 carbon atoms which may contain at least one hetero atom, a pair of $R^2$ and $R^3$ may bond together to form a ring with the carbon atom to which they are bonded, and each of $R^2$ and $R^3$ is a divalent hydrocarbon group of 1 to 15 carbon atoms which may contain at least one hetero atom when they form a ring, $R^4$ is hydrogen, hydroxyl, or a monovalent hydrocarbon group of 1 to 15 carbon atoms which may contain at least one hetero atom, $R^6$ is a protective group, and Z is such a monovalent group that $R^4$—Z provides a $R^4$ anion equivalent.

4. A process for preparing a polymerizable fluorinated ester compound having the general formula (2), comprising the steps of reacting a ketoalcohol compound having the general formula (3) with a compound of the general formula: $R^4$—Z to form a diol compound having the general formula (4), protecting the diol compound with an acid labile group to form an alcohol compound having the general formula (7), and acylating the alcohol compound to form a polymerizable fluorinated ester compound having the general formula (2):

wherein $R^1$ is hydrogen, methyl or trifluoromethyl, $R^2$ and $R^3$ are each independently hydrogen or a monovalent hydrocarbon group of 1 to 15 carbon atoms which may contain at least one hetero atom, a pair of $R^2$ and $R^3$ may bond together to form a ring with the carbon atom to which they are bonded, and each of $R^2$ and $R^3$ is a divalent hydrocarbon group of 1 to 15 carbon atoms which may contain at least one hetero atom when they form a ring, $R^4$ is hydrogen, hydroxyl, or a monovalent hydrocarbon group of 1 to 15 carbon atoms which may contain at least one hetero atom, $R^5$ is an acid labile group, and Z is such a monovalent group that $R^4$—Z provides a $R^4$ anion equivalent.

5. A process for preparing a polymerizable fluorinated ester compound having the general formula (2), comprising the step of protecting a polymerizable fluorinated ester compound having the general formula (1) with an acid labile group to form a polymerizable fluorinated ester compound having the general formula (2):

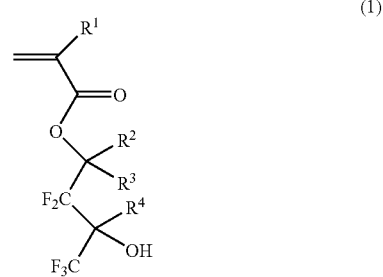

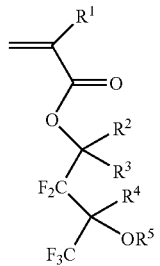

(2)

wherein $R^1$ is hydrogen, methyl or trifluoromethyl, $R^2$ and $R^3$ are each independently hydrogen or a monovalent hydrocarbon group of 1 to 15 carbon atoms which may contain at least one hetero atom, a pair of $R^2$ and $R^3$ may bond together to form a ring with the carbon atom to which they are bonded, and each of $R^2$ and $R^3$ is a divalent hydrocarbon group of 1 to 15 carbon atoms which may contain at least one hetero atom when they form a ring, $R^4$ is hydrogen, hydroxyl, or a monovalent hydrocarbon group of 1 to 15 carbon atoms which may contain at least one hetero atom, and $R^5$ is an acid labile group.

* * * * *